United States Patent [19]

Ballou et al.

[11] Patent Number: 5,198,360
[45] Date of Patent: Mar. 30, 1993

[54] DNA SEQUENCE CONFERRING A PLAQUE INHIBITION PHENOTYPE

[75] Inventors: Margaret M. Ballou; Richard H. Baltz; Margaret A. McHenney, all of Indianapolis, Ind.

[73] Assignee: Eli Lilly and Company, Indianapolis, Ind.

[21] Appl. No.: 467,452

[22] Filed: Jan. 19, 1990

[51] Int. Cl.$^5$ .................. C12N 1/20; C12N 15/11; C12N 15/00

[52] U.S. Cl. .................. 435/252.3; 435/252.35; 435/320.1; 536/23.72; 935/38; 935/42

[58] Field of Search ........... 435/70.1, 71.3, 252.35, 435/259; 935/38, 42

[56] References Cited

FOREIGN PATENT DOCUMENTS 88301763.4 7/1988 European Pat. Off. .

OTHER PUBLICATIONS

Baltz and McHenney, *Genetics and Molecular Biology of Industrial Microorganisms* (American Soc. for Microbiol., ed. Hershberger, Queener, and Hegeman, 1989) pp. 163–167.

Baltz, R., Horizons on Antibiotic Research (Jap. Antibiot. Research Assoc., ed. Davis, Ishikawa, Maeda, Mischer, 1988) pp. 228–237.

McHenney, M., and Baltz, R., 1989, J. Antibiotics, vol. XLII No. 11, pp. 1725–1727.

Matsushima, P., McHenney, M., and Baltz, R., 1989, J. Bacteriol. vol. 171:3080–3084.

McHenney, M., and Baltz, R., 1988, J. Bacteriol., vol 170:2276–2282.

Cox, K., Ballou, M., and Seno, E., Fourth A.S.M. Conference on the Genetics and Molecular Biology of Industrial Microorganisms, Bloomington, Ind., Oct. 2–5, 1988.

Cox, K., and Baltz, R., 1984, J. Bacteriol., vol. 159:499–504.

Primary Examiner—Elizabeth C. Weimar
Assistant Examiner—Deborah Crouch
Attorney, Agent, or Firm—John E. Parrish; Leroy Whitaker; Robert A. Conrad

[57] ABSTRACT

The present invention comprises an ~0.8 kb Sac II restriction fragment of phage FP43, which confers the pin phenotype. The present invention allows transduction at high m.o.i. using the phage FP43 high frequency transduction system.

13 Claims, 11 Drawing Sheets

DNA SEQUENCE CONFERRING A PLAQUE INHIBITION PHENOTYPE

BACKGROUND OF THE INVENTION

The application of recombinant DNA technology to industrially important organisms such as Streptomyces and related actinomycete genera requires efficient gene cloning and transformation procedures.

Transformation of Streptomyces and related genera is well known in the art. Transformation of Streptomyces and related genera using standard transformation procedures requires that the recipient cells be enzymatically converted to protoplasts. Several drawbacks to the protoplast transformation methods have, however, impeded the wide application of recombinant DNA technology in many species of Streptomyces and related genera. First, the protocols required for efficient transformation vary greatly, and subtle procedural details often need to be worked out before productive cloning experiments can proceed. Compare the transformation procedure of Matsushima et al., 1985, J. Bacteriol. 163: 180–185 with that of Yamamoto et al. 1986, J. Antibiotics 39: 1304–1313. Second, most Streptomycetes produce restriction endonucleases (see Cox and Baltz, 1984, J. Bacteriol. 159: 499–504 and Lomovskaya et al., 1980, Microbiol. Rev. 44: 206–229) that can decrease the efficiency of phage infection and plasmid transformation. See Matsushima and Baltz, 1985, J. Bacteriol. 163: 180–185; Chater and Wilde, 1980, J. Gen. Microbiol. 116: 323–334; Chater and Wilde, 1976, J. Bacteriol. 128: 644–680; and Chater and Carter, 1978, J. Gen. Microbiol. 109: 181–185. The problem caused by restriction endonucleases is often compounded by the rigid procedural requirements for efficient uptake of plasmid DNA and protoplast regeneration. Physiological conditions for cell growth that might minimize the expression of restriction endonucleases often inhibit efficient uptake of DNA, plasmid replication, and protoplast regeneration.

A bacteriophage-mediated transduction system circumvents many of the problems encountered in protoplast transformation procedures. In a transduction system, the transducing DNA can be packaged into phage particles, which can attach and inject DNA, and thus, transduce intact cells, thereby avoiding the need to prepare and regenerate protoplasts. Intact cells can tolerate a broader range of culture conditions, especially temperature of incubation, better than protoplasts. A transduction system can circumvent the problems encountered with host restriction systems, because some host restriction systems may become less active as the temperature of incubation varies from that of optimal growth. In addition, a transduction system can be used simply to overwhelm host restriction systems, for by raising the multiplicity of infection (m.o.i.), one increases the amount of transducing DNA introduced into a cell. Finally, phage-mediated transduction can be used to transform different strains of the same species and even other species and genera. Plasmid-mediated transformation systems, however, are often limited by the narrow host range of the transforming plasmid. The significant advantages inherent in a transduction system are presently limited in their useful scope of applications by the necessity of using a low m.o.i. to prevent lysis of the recipient cells by intact phages.

The present invention provides DNA compounds which were isolated from phage FP43 and which confer a plaque inhibition pin phenotype on cells comprising the pin sequence. Thus, host cells comprising the pin sequence are transducible at high m.o.i.

BRIEF DESCRIPTION OF THE DRAWINGS

The figures described below are drawn to scale; however, observed restriction fragment size may vary somewhat from calculated size based on map distances. For some restriction enzymes, only certain cut sites are shown for convenience.

SUMMARY OF THE INVENTION

The present invention provides a significant improvement in bacteriophage FP43-mediated transduction systems, which are useful not only for Streptomyces but also for other organisms throughout the Actinomycetates family, such as Chainia, Saccharopolyspora, and Streptoverticillium. Bacteriophage FP43-mediated transduction is particularly useful because of the broad host range of phage FP43. Phage FP43-mediated transduction of recombinant DNA vectors allows for the introduction of DNA into high a percentage of Streptomyces species and many other heretofore untransformable organisms. Streptomyces provides over half of the clinically important antibiotics and thus is a commercially significant group.

Recombinant DNA vectors of the present invention comprise a segment of DNA isolated from the phage FP43 genome, which confers plaque inhibition phenotype (pin). Host cells which comprise the pin sequence are transducible at high m.o.i., with phage FP43-mediated transduction. The ability to transduce at high m.o.i. greatly facilitates the exploitation of Streptomyces and related genera by recombinant DNA technology. Significantly greater quantities of recombinant DNA can be transduced into the pin-containing host cells of the invention. Thus genetic manipulations, which heretofore were encumbered by the low frequencies associated with, for example, homologous recombination of cloned DNA into the host cell, are readily performable using the pin conferring DNA compounds of the present invention.

Thus the present invention provides DNA compounds comprising the pin sequence, recombinant DNA vectors that comprise the pin sequence, and host cells of the pin phenotype by virtue of their containing recombinant DNA vectors comprising the pin sequence.

DETAILED DESCRIPTION

The present invention comprises DNA compounds that comprise the pin sequence of phage FP43. An approximately 0.8 kb fragment of DNA isolated from phage FP43 comprises the pin sequence. The pin sequence confers resistance to phage FP43 lysis when host cells are transformed with recombinant DNA vectors comprising the pin sequence.

Figure 1:
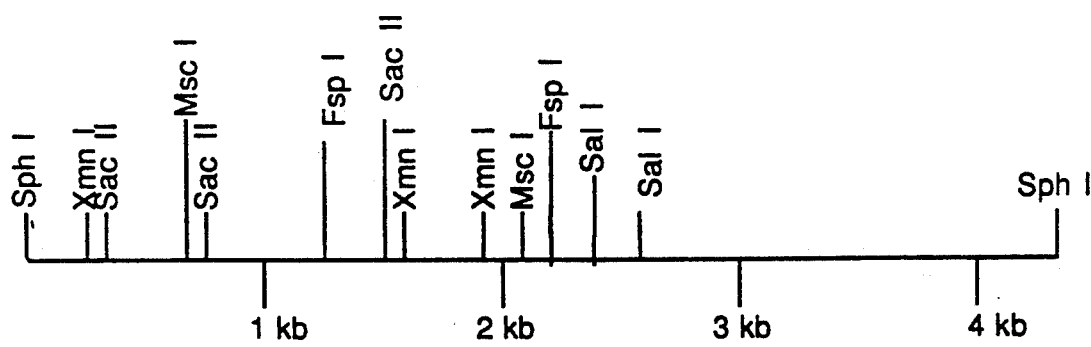
FIG. 1 is a restriction map of the ~4.3 kb Sph I fragment isolated from phage FP43.

An ~4.3 kb SphI fragment isolated from phage FP43 was used to construct several illustrative recombinant DNA vectors. *Streptomyces griseofuscus* (FP43) is available from the Northern Regional Research Center (NRRL), Agricultural Research Service, U.S. Department of Agriculture, Peoria, Ill., 61604, under the accession number NRRL 18184. Cultivation of accession number 18184 and isolation of phage FP43 therefrom is described in Example 1. A restriction map of the ~4.3 Sph I restriction fragment of phage FP43 is provided in FIG. 1. Thus, phage FP43 is a source of the DNA compounds of the present invention.

Figure 2:
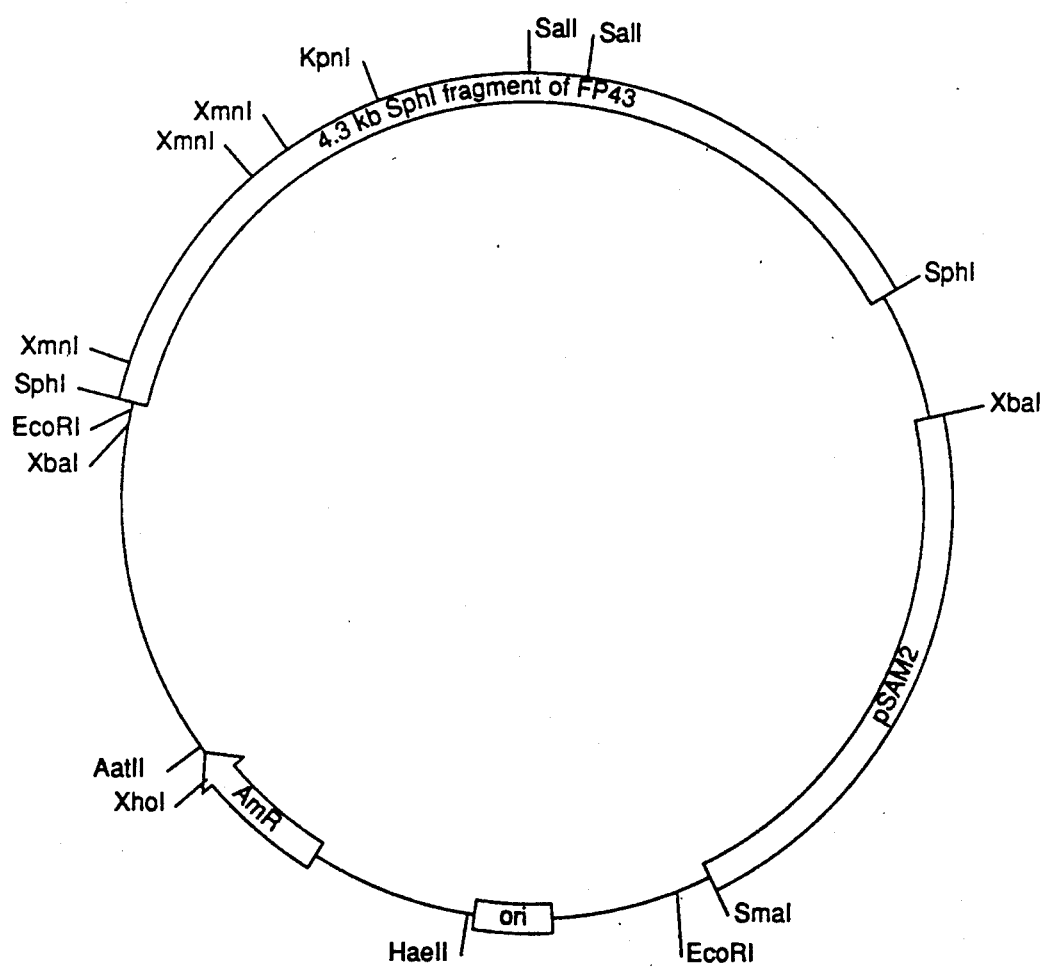
FIG. 2 is a restriction site and function map of plasmid pKC684.

A preferred source of the DNA compounds of the present invention is plasmid pKC684. *Escherichia coli* DH5 α/pKC684 has been deposited in the NRRL and is available under the accession number NRRL B-18541. Plasmid pKC684 comprises a Streptomyces replicon, an integration sequence derived from plasmid pSAM2, an *E. coli* replicon, and an apramycin resistance marker. A restriction site and function map of plasmid pKC684 is provided in FIG. 2. Plasmid pKC684 illustrates an important aspect of the present invention. Transformation of host cells with illustrative plasmid pKC684 results in integration of plasmid pKC684 into the host cell chromosome. The integration of the pin sequence into the host cell chromosome is a preferred embodiment of the present invention. Integration of the pin sequence into the host cell chromosome provides for the stable maintenance of the pin phenotype in the transformed host cell as well as all subsequent progeny thereof. Host cells comprising an integrated pin sequence are immune to lysis by phage FP43. The immunity to lysis by phage FP43 allows high m.o-.i.'s to be utilized in the phage FP43-mediated transductions.

Plasmids which comprise the pin sequence, yet lack the ability to integrate into the host cell chromosome represent another important embodiment of the present invention. Plasmid pKC703 illustrates the utility of a plasmid, which comprises the pin sequence but does not integrate. Plasmid pKC703 is especially useful because of its instability. Transformation of Streptomyces and related genera with plasmid pKC703 confers immunity to phage FP43 lysis. Apramycin (Am) selection of host cells transformed with plasmid pKC703 is required to maintain plasmid pKC703. When antibiotic selection is removed, plasmid pKC703 is lost from >99.9% of the cells.

Host cells transformed with pKC703 are readily transducible with the hft transduction system at a high m.o.i. Hft transduction refers to the use of vectors comprising the hft sequence to transduce DNA into Streptomyces and related genera at a high frequency. Host cells are protected from FP43 lysis as long as plasmid pKC703 is present in the host cells. After the transduction, the removal of antibiotic results in curing the host cells of plasmid pKC703. Thus, plasmid pKC703 can transiently protect host cells from phage FP43 lysis during hft transduction procedures. Removal of antibiotic selection after the transduction results in curing the cells of plasmid pKC703 and leaves the transduced host cells free of the metabolic burden of maintaining an unneeded plasmid.

Figure 8:
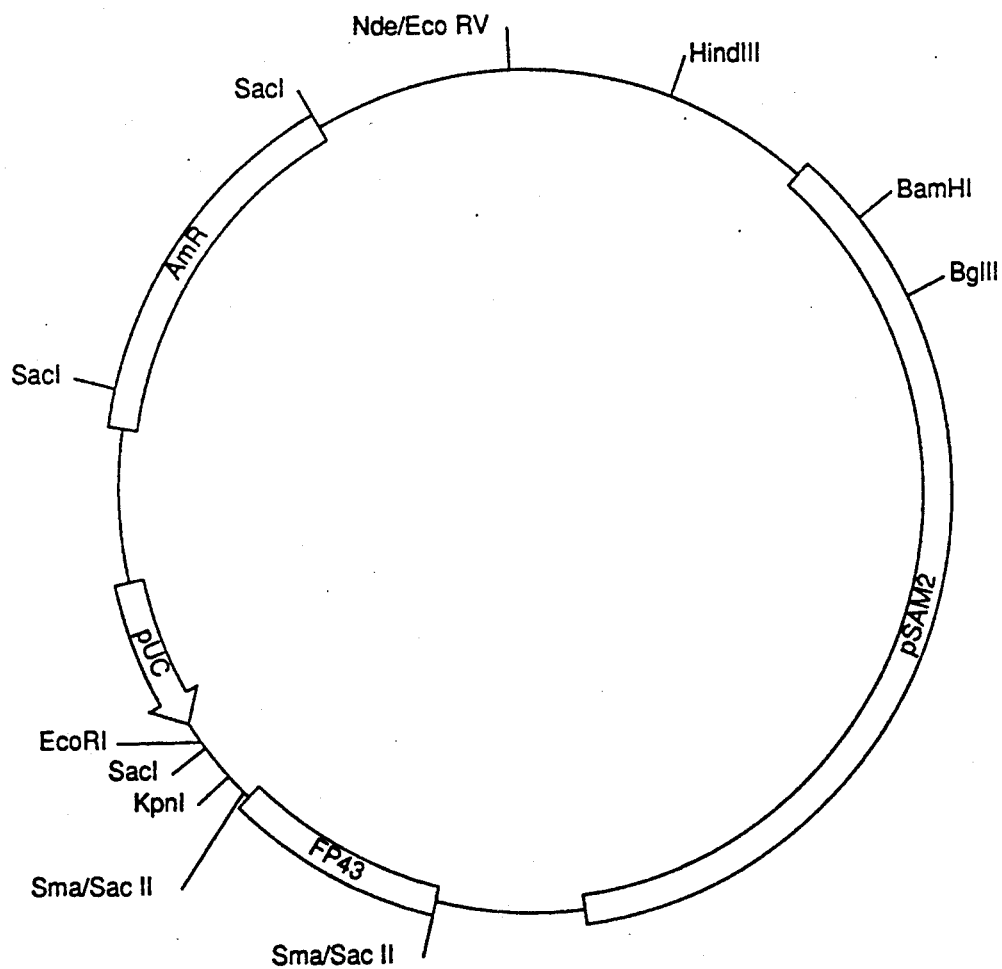
FIG. 8 is a restriction site and function map of plasmid pKC-XS.
Figure 9:
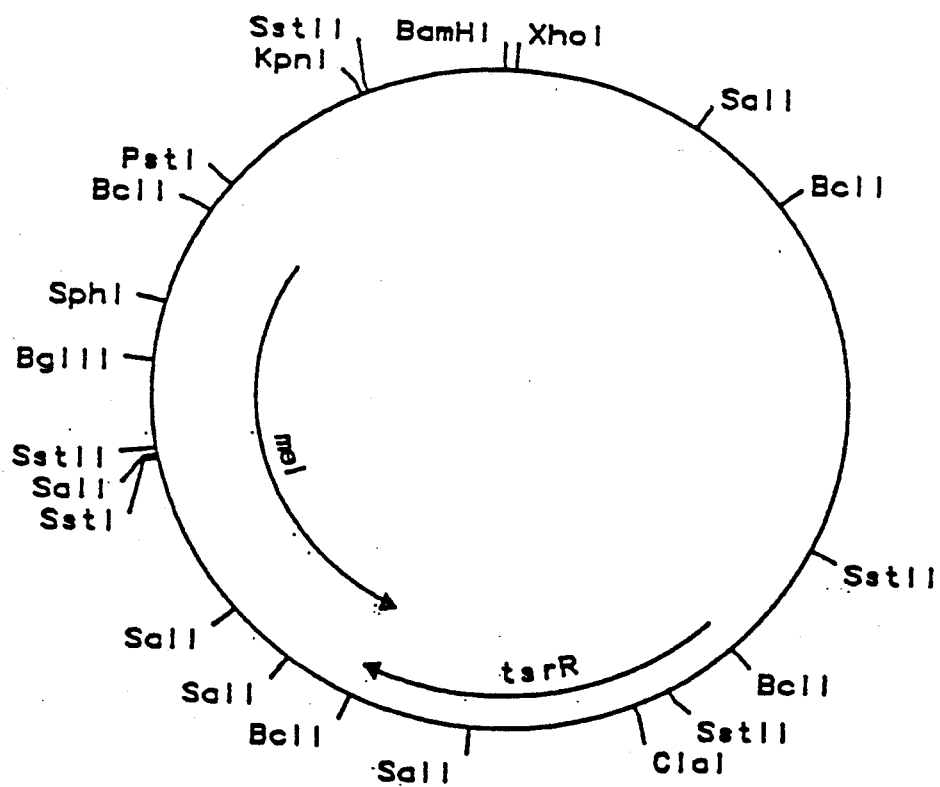
FIG. 9 is a restriction site and function map of plasmid pIJ702.
Figure 10:
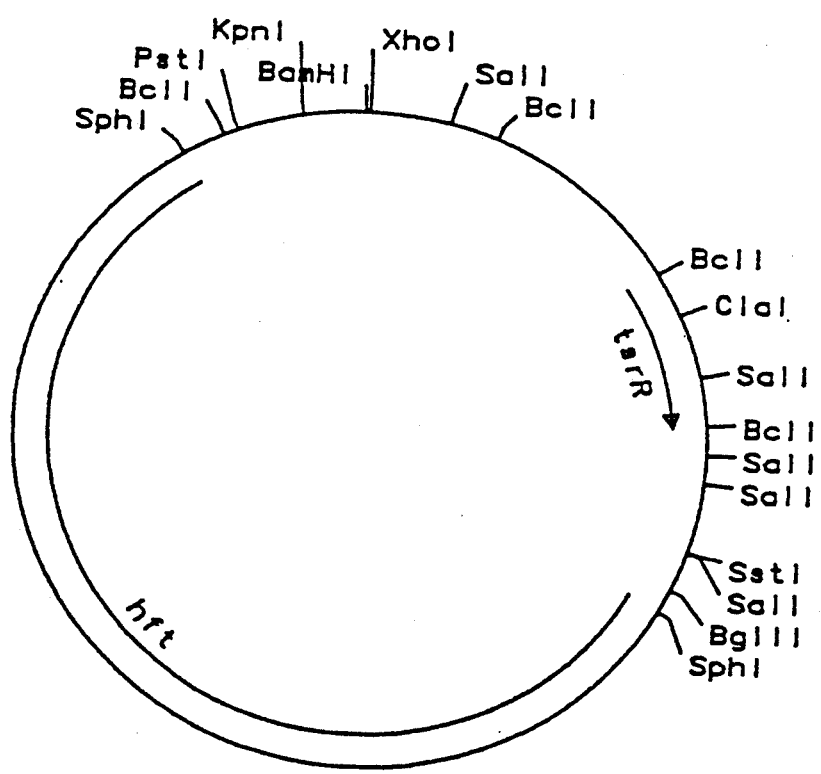
FIG. 10 is a restriction site and function map of plasmid pRHB101.

The preceding illustrative embodiments of the pin sequence host utilized the ~4.3 kb SphI fragment of phage FP43. Further useful recombinant DNA vectors have been constructed with the pin sequence localized to an ~0.8 kb pin containing fragment. A restriction site and function map of plasmid pKC-XS is provided in FIG. 8. Construction of plasmid pKC-XS is taught in Example 14. When host cells transformed with plasmid pKC-XS were challenged with phage FP43 no lysis was observed. The absence of lysis by phage FP43 illustrates the function of the ~0.8 kb fragment.

The ~0.8 kb pin sequence is a preferred embodiment of the present invention. The ~0.8 kb pin fragment can be further reduced in size by skills well known in the art. A restriction map of the ~4.3 kb SphI fragment of phage FP43 is provided in FIG. 1. Thus, the teachings of the present invention enable the derivation of pin sequences smaller than ~0.8 kb.

The vectors disclosed to illustrate the various utilities of the pin sequence are merely representative of the recombinant DNA vectors which can be constructed. Other Streptomyces replicons available to construct further recombinant DNA vectors comprising pin sequence include, but are not limited to those listed in Table 1.

TABLE 1

Streptomyces Plasmids

| Plasmid | Host | Accession Number |
|---------|------|------------------|
| SCP2 | *Streptomyces coelicolor* A3(2) | NRRL 15042 |
| SCP2* | *Streptomyces coelicolor* M110 | NRRL 15041 |
| pEL7 | *Streptomyces ambofaciens*/pEL7 | NRRL 12523 |
| pUC6 | *Streptomyces espinosus* | NRRL 11439 |
| pUC3 | Streptomyces 3022A | NRRL 11441 |
| SLP1 | *Streptomyces lividans* | NCIB[1] 11417 |
| pNM100 | *Streptomyces virginiae* | NRRL 15156 |
| pEL103 | *Streptomyces granuloruber* A399 12.13/pEL103 | NRRL 12549 |
| pIJ702 | *Streptomyces lividans* | ATCC[2] 39155 |

[1]National Collection of Industrial Bacteria (NCIB), Torry Research Station, Post Office Box 31, 135 Abbey Road, Aberdeen AB98DG, Scotland, United Kingdom.
[2]American Type Culture Collection, Rockville, MD 20852.

Restriction fragments used to construct vectors illustrative of the present invention can be conventionally modified to facilitate ligation. For example, molecular linkers can be provided to a particular pin-containing restriction fragment or to DNA comprising vector replication functions. Thus, specific sites for subsequent ligation can be conveniently constructed.

It is also noteworthy that a given pin-containing restriction fragment is not limited to a particular position on a cloning vector, as long as critical, vector-controlled functions are not disrupted. Those skilled in the art understand or can readily determine which sites on a vector are advantageous for the ligation or insertion of a particular pin-containing restriction fragment.

The development of the high frequency transduction system utilizing phage FP43-mediated transduction marked a significant advance in the art of the molecular biology of Streptomyces and related genera. The FP43 transduction sequence was disclosed and claimed in U.S. patent application No. 07/020,807, filed Mar. 2, 1987. The corresponding European Patent Application number 88301763.4 was published on Sep. 7, 1988. The pin sequence provided in the present invention further extends the utility of the FP43 hft.

Figure 11:
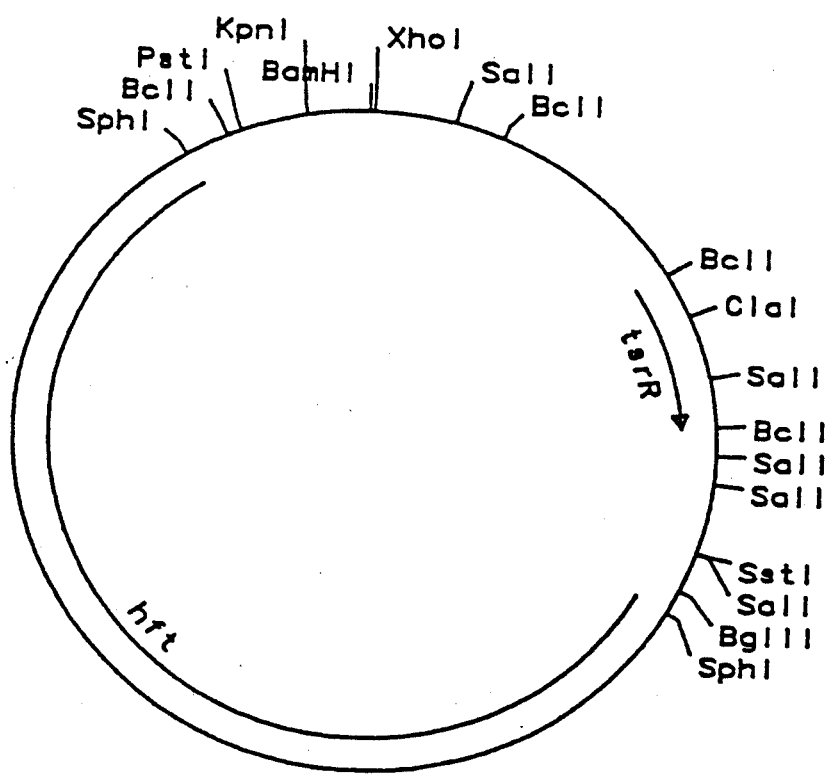
FIG. 11 is a restriction site and function map of plasmid pRHB106.

Recombinant DNA vectors that comprise the phage FP43 hft sequence and thus are benefitted by the pin sequence of the present invention are illustrated by plasmid pRHB106. Streptomyces griseofuscus/pRHB106 has been deposited in the NRRL and is available under the accession number NRRL 18183. A restriction site and function map of plasmid pRHB106 is provided in FIG. 11. Plasmid pRHB106 was prepared by inserting the ~7.8 kb SphI fragment of phage FP43 into SphI digested plasmid pMT660.

Plasmid pRHB101 is another illustrative recombinant DNA vector comprising the hft sequence of phage FP43. Plasmid pRHB101 was prepared by digesting plasmid pRHB106 with SphI, isolating the ~7.8 SphI fragment comprising the FP43 hft sequence, and ligating the hft sequence into SphI digested plasmid pIJ702. Plasmid pIJ702 is a multicopy plasmid about 5.8 kb in size that has broad host specificity for Streptomyces (see Acebal et al., 1986, FEMS Microbiol. Lett. 35: 79–82; Katz et al., 1982, J. Gen. Microbiol. 192: 2703–2714; Lampel and Strohl, 1986, Appl. Environ. Microbiol. 51: 126–131; and Matsushima and Baltz, 1985, J. Bacteriol. 163: 180–185) and also replicates in *Amycolatopsis orientalis, Saccharopolyspora erythraea* (see Yamamoto et al., 1986, J. Antibiol. 39: 1304–1313), and *Thermomonospora fusca* (see Pidcock et al., 1985, Appl. Environ. Microbiol. 50: 693–695). Plasmid pIJ702 was derived from the multicopy, broad host range plasmid pIJ101 (Kieser et al., 1982, Mol. Gen. Genet. 185: 223–238) and can be obtained from the American Type Culture Collection, Rockville, Md. 20852, under the accession number ATCC 39155. A restriction site and function map of plasmid pIJ702 is presented in FIG. 11 of the accompanying drawings.

The construction of plasmid pRHB101 from the ~7.8 kb SphI restriction fragment of phage FP43 and SphI-digested plasmid pIJ702 is described in Example 2, below. A restriction site and function map of plasmid pRHB101 is presented in FIG. 12 of the accompanying drawings.

The illustrative recombinant DNA vectors resulting from the insertion of phage FP43 DNA into the SphI site of plasmids pIJ702 and pMT660 were transformed into *Streptomyces lividans*, and thiostrepton-resistant, white transformants were isolated. Plasmid DNA was isolated from the transformants to confirm the presence of DNA inserts. Plasmids containing inserts of FP43 DNA were transformed into *S. griseofuscus* and *S. ambofaciens*, and FP43 lysates were prepared on the transformants. The lysates were used to transduce a plasmid into wild-type *S. griseofuscus* and *S. ambofaciens*, and thiostrepton-resistant transductants were counted. The ~7.8 kb SphI restriction fragment of FP43 (designated hft for high frequency transduction) caused at least a $10^5$-fold increase, as compared with plasmid pIJ702 with no insert, in transduction in *S. griseofuscus*, as demonstrated in Table 2, below.

TABLE 2

Effects of FP43 DNA inserts on transduction of plasmids pIJ702 and pMT660

| Plasmid | Original Vector | Insert size (kb) | Transduction frequency[a] S. ambofaciens | S. griseofuscus |
|---|---|---|---|---|
| pRHB101 | pIJ702 | 7.8 | | $4.0 \times 10^{-4}$ |
| pRHB102 | pIJ702 | 6.9 | $1.7 \times 10^{-6}$ | |
| pRHB103 | pIJ702 | 2.4 | | $<1.4 \times 10^{-8}$ |
| pRHB104 | pIJ702 | 1.4 | $3.1 \times 10^{-6}$ | |
| pRHB105 | pIJ702 | 2.9 | $<5.0 \times 10^{-7}$ | |
| pRHB106 | pMT660 | 7.8 | | $4.0 \times 10^{-4}$ |
| pRHB107 | pMT660 | 1.5 | | $<4.5 \times 10^{-9}$ |
| pRHB108 | pMT660 | 0.9 | | $<8.3 \times 10^{-7}$ |
| pRHB109 | pMT660 | 1.0 | | |
| pRHB110 | pMT660 | 4.1 | | $<7.7 \times 10^{-6}$ |
| pIJ702 | — | | | $<2.2 \times 10^{-8}$ |
| pMT660 | — | | | $<2.2 \times 10^{-9}$ |

[a]The ratio of the number of transductants to the number of PFU determined on *S. griseofuscus*.

The average transduction frequency obtained was about $10^{-4}$ per plaque-forming unit. No transduction ($<2.2 \times 10^{-9}$ per PFU) was observed with plasmid pIJ702 containing no inserts. As indicated in Table 2, other plasmids containing inserts of FP43 DNA gave transduction frequencies only slightly higher than observed for plasmid pIJ702.

The hft system differs from other transduction systems, because the hft segment can be transduced into most species of Streptomyces. Lysates of phage FP43 prepared on *S. griseofuscus* containing plasmid pRHB101 and *S. griseofuscus* containing plasmid pRHB106 were used to transduce many other species of Streptomyces, including both species that do and do not support plaque-formation by FP43. Of the species tested that do not support plaque-formation, some express restriction endonucleases that cleave FP43 DNA (see Cox and Baltz, 1984, J. Bacteriol. 159: 499–504). Of the 13 species tested that support plaque-formation by FP43, only one, *Streptomyces lavendulae*, was not transduced to thiostrepton resistance by FP43. The results of these transductions are presented in Table 3.

TABLE 3

Interspecies transduction of plasmid pRHB101 by bacteriophage FP43 is Streptomyces

| Strain | Plaque formation | Transduction | [a]Transduction Frequency |
|---|---|---|---|
| *S. albus* P | + | + | $2.8 \times 10^{-6}$ |
| *S. albus* J1074 | + | + | $6.1 \times 10^{-8}$ |
| *S. ambofaciens* | + | + | $4.5 \times 10^{-5}$ |
| *S. aureofaciens* | + | + | $1.3 \times 10^{-7}$ |
| *S. cinnamonensis* | + | + | $7.3 \times 10^{-6}$ |
| *S. fradiae* PM73 | + | + | $1.8 \times 10^{-7}$ |
| *S. fradiae* M1 | + | + | |
| *S. griseofuscus* | + | + | $9.6 \times 10^{-4}$ |
| *S. griseus* | + | + | $3.2 \times 10^{-7}$ |
| *S. macrosporeus* | + | + | $1.1 \times 10^{-6}$ |
| *S. parvulus* | + | + | $8.7 \times 10^{-7}$ |
| *S. tubercidicus* | + | + | $2.3 \times 10^{-7}$ |
| *S. tennebrarius* E | + | + | $1.2 \times 10^{-4}$ |
| *S. lavendulae* | + | − | $<2.9 \times 10^{-9}$ |
| *S. coelicolor* | − | + | $1.9 \times 10^{-5}$ |
| *S. felleus* | − | + | $5.7 \times 10^{-6}$ |
| *S. lividans* | − | + | $3.5 \times 10^{-5}$ |
| *S. phaeochromogenes* | − | + | $8.5 \times 10^{-9}$ |
| *S. thermotolerans* | − | + | $5.0 \times 10^{-6}$ |
| *S. venezuelae* | − | + | $1.0 \times 10^{-5}$ |
| *S. cirratus* | − | + | $2.0 \times 10^{-7}$ |
| *S. acromogenes* | − | − | $<4.3 \times 10^{-9}$ |
| *S. albus* G | − | − | $<1.3 \times 10^{-10}$ |
| *S. fungicidicus* | − | − | $<2.5 \times 10^{-8}$ |

TABLE 3-continued

Interspecies transduction of plasmid pRHB101
by bacteriophage FP43 is Streptomyces

| Strain | Plaque formation | Transduction | *Transduction Frequency |
|---|---|---|---|
| S. narbonensis | — | — | <2.5 × 10$^{-8}$ |

*The ratio of the number of transductants to the number of PFU determined on S. griseofuscus.

The species transduced included S. albus P, which produces SalPI, an isoschizomer of PstI. Plasmids pRHB101 and pRHB106 contain one site for PstI, so the present system provides a means of overcoming such restriction systems. Table 3 also shows that the transduction system of the present invention can even be used to transform organisms resistant to phage FP43 infection. Of the 11 Streptomyces species that do not support plaque-formation by FP43, seven can be transduced to thiostrepton resistance by FP43. Therefore, FP43 clearly attaches and injects DNA into these species, as predicted from the host range analysis. (See Cox and Baltz, 1984, J. Bacteriol. 159: 499-504). Phage FP43 is probably restricted to a much greater extent in these species than plasmids pRHB101 and pRHB106. For instance, FP43 has many sites for SphI produced by S. phaeochromogenes and is completely restricted, whereas plasmid pRHB101 has only two sites for SphI and transduces at low but detectable frequency of $8.5 \times 10^{-9}$ per plaque-forming unit.

FP43, like other Streptomyces phages (Chater, K., 1986, Streptomyces phages and their applications to Streptomyces genetics, p. 119-158, In S. W. Queener and L. E. Day (eds.), The Bacteria Vol. IX, Antibiotic-producing Streptomyces. Academic Press, New York.) has broad host specificity. Baltz and Cox, 1984, J. Bacteriol. 159: 499-504, demonstrated that phage FP43 formed plaques on 14 of 30 species tested, and the data suggested that the lack of plaque-formation on the 16 species was due primarily to host restriction endonuclease systems. Phage FP43 does not form plaques on S. albus G, S. acromogenes, or S. phaeochromogenes, the producers of restriction endonucleases SalI, SacI, and SphI, respectively; FP43 DNA has many sites for all three enzymes. FP43 forms plaques on S. albus P and S. tubercidicus, the producers of SalPI (PstI) and StuI, respectively; FP43 DNA has no PstI or StuI sites. These observations suggest that FP43 might attach to and inject DNA into most, if not all, species of Streptomyces. The absence of plaque formation by phage FP43 on some Streptomyces species represents host restriction rather than a failure of phage FP43 to attach to and inject DNA into the host cells. The present transduction system provides a convenient means for avoiding such restriction systems.

If FP43 packaged a plasmid containing a relatively small number of restriction sites, it might transduce that plasmid into a strain that is highly restricting for FP43. Of the strains listed in Table 3, Streptomyces griseofuscus, S. ambofaciens, S. lividans, S. parvulus, and S. albus J1074 are relatively non-restricting; S. albus G (SalI), S. lavendulae (SlaI), S. phaeochromogenes (SphI), S. acromogenes (SacI, SacII), and S. tubercidicus (StuI) produce well characterized restriction systems (shown in parenthetical remark following the strain name); and strains S. aureofaciens, S. cirratus, S. coelicolor, S. griseus, S. narbonensis, S. thermotolerans, S. venezuelae, and S. macrosporeus are suspected of producing restriction systems. The transduction system of the invention works well in 13 of the 14 strains tested that FP43 forms plaques on and works well in 7 of 11 strains that FP43 does not form plaques on. Four of the five strains that were not transduced produce potent restriction systems; S. albus G produces SalI, an enzyme that cuts plasmid pRHB101 five times. Only about 20% of the strains tested produce restriction systems that are not readily bypassed.

Two of the species transduced produce well-characterized enzymes that produce restriction endonucleases that cut the transducing plasmid. S. albus P produces SalPI, an isoschizomer of PstI that cuts plasmid pRHB101 one time, and S. phaeochromogenes produces SphI, which cuts plasmid pRHB101 two times. Phage FP43 transduced S. albus P and S. phaeochromogenes at frequencies about 10$^2$-fold and 10$^4$-fold lower than those obtained on the nonrestricting S. griseofuscus. In the case of S. albus P, the relative transduction frequency was improved 100-fold by preparing the transducing lysate in S. albus P. It appears, therefore, that the plasmid was efficiently modified for the SalPI restriction system after replication in S. albus P. This procedure can be used in other species to improve transduction efficiencies and is believed to work by a mechanism involving modification (i.e., methylation) of the transducing DNA by the modifying organism (S. albus P in the procedure above).

This modifying procedure was carried out by transducing S. albus P to thiostrepton resistance using an FP43 lysate prepared on S. griseofuscus containing plasmid pRHB101. A subsequent FP43 lysate was prepared on S. albus P containing plasmid pRHBl01. The two transducing lysates were compared for their relative abilities to transduce S. griseofuscus and S. albus P strains not containing plasmid. Table 4, below, shows that the lysate prepared on S. griseofuscus transduced S. albus P to thiostrepton resistance about 1.5% as efficiently as it transduced native S. griseofuscus. The lysate prepared on S. albus P, however, transduced both species at about equal efficiencies. Thus passaging the plasmid through the restricting host increased the relative transduction on the restricting host by about 100-fold.

TABLE 4

Transduction of Streptomyces griseofuscus and S. albus P host with FP43 lysates prepared on S. griseofuscus/pRHB101 or S. albus P/pRHB101

| Source of transducing lysate | Transduction frequency on | | Relative Transduction (S. albus/ S. griseofuscus) |
|---|---|---|---|
| | S. griseofuscus | S. albus P | |
| S. griseofuscus | 6.6 × 10$^{-4}$ | 1.0 × 10$^{-5}$ | 0.015 |
| S. albus P | 2.4 × 10$^{-5}$ | 3.5 × 10$^{-5}$ | 1.5 |

The very high frequency of successful transductions obtained in Streptomyces species that do not support FP43 plaque-formation suggested that the lack of plaque-formation by Streptomyces phages in other actinomycete genera is due to events beyond phage attachment and injection and that the FP43 transduction system of the present invention could be used to transduce other actinomycete genera. Intergeneric transductions can also be facilitated by using plasmids with very broad host ranges; plasmid pIJ702 and derivatives replicate not only in Streptomyces but also in Saccharopolyspora, Amycolatopsis, and Thermomonospora species.

Lysates of phage FP43 prepared on S. griseofuscus/pRHB101 were mixed with cells prepared from several species of different actinomycete genera, and plaque-formation and transduction scored. The results are presented in Table 5, below.

TABLE 5

Intergeneric transduction of plasmid pRHB101 by bacteriophage FP43

| Strain | Plaque formation | Transduction | [a]Transduction Frequency |
|---|---|---|---|
| *Chainia minutisclerotica* ATCC 19346 | + | + | $1.1 \times 10^{-6}$ |
| *Chainia ochracea* ATCC 15814 | − | + | $6.1 \times 10^{-7}$ |
| *Chainia olivacea* ATCC 15722 | − | + | $4.1 \times 10^{-8}$ |
| *Saccharopolyspora erythraea* ATCC 11635 | − | + | $6.0 \times 10^{-7}$ |
| *Saccharopolyspora hirsuta* ATCC 27875 | − | + | $1.4 \times 10^{-8}$ |
| *Streptoverticillium oliverticulli* ATCC 23943 | + | + | $7.1 \times 10^{-9}$ |
| *Streptoverticillium kentuckense* NRRL B-1831 | − | + | $2.1 \times 10^{-7}$ |
| *Streptoverticillium albireticuli* NRRL B-1670 | − | − | $<7.1 \times 10^{-10}$ |

[a]The ratio of the number of transductants to the number of PFU determined on *S. griseofuscus*.

FP43 caused plaque-formation on *Streptoverticillium oliverticulli* and *Chainia minutisclerotica*. However, transduction was successful not only in Streptoverticillium and Chainia, but also in Saccharopolyspora. These results indicate that FP43 can attach and inject plasmid DNA into a variety of actinomycete genera and that plasmid pRHB101 can establish and replicate in many different genera. Thus, the transduction system described here provides a very powerful technique to move cloned genes between a variety of Streptomyces species and into at least several other actinomycete genera and eliminates the need to develop transformation systems for each species of interest. This should accelerate the applications of recombinant DNA technology in actinomycetes to produce novel or hybrid antibiotics.

The wide host range of the transduction vectors comprising an hft sequence provides an enormous advantage over protoplast-transformation in experiments and procedures for transferring genes from one organism to another. Because this transduction system works in such a diversity of organisms, the optimal conditions for transducing one organism may differ from the optimal conditions for transforming a different organism. One condition that can be optimized is the multiplicity of infection (m.o.i.).

To understand how m.o.i. and transduction efficiency are related, it is important to understand transduction. To make a transducible plasmid, the hft sequence of phage FP43 is incorporated into a recombinant DNA expression vector. That vector (i.e., plasmid pRHB101 or plasmid pRHB106) is then transformed, by conventional protoplast-transformation procedures, into an organism, such as *Streptomyces griseofuscus* C581 (ATCC 23916). The resulting transformants are then infected with phage FP43. Upon phage infection, plasmids containing the hft sequence are replicated and packaged into phage heads. The resulting lysate contains noninfective particles that have packaged the hft-containing plasmid DNA.

The resulting lysate also contains, however, infective phage particles that have packaged the phage FP43 genome. These "wild-type" infective particles can cause lysis, and are thus referred to as "plaque-forming units" or "PFU", of the recipient host cells when the lysate is used in a subsequent transduction.

Figure 4:
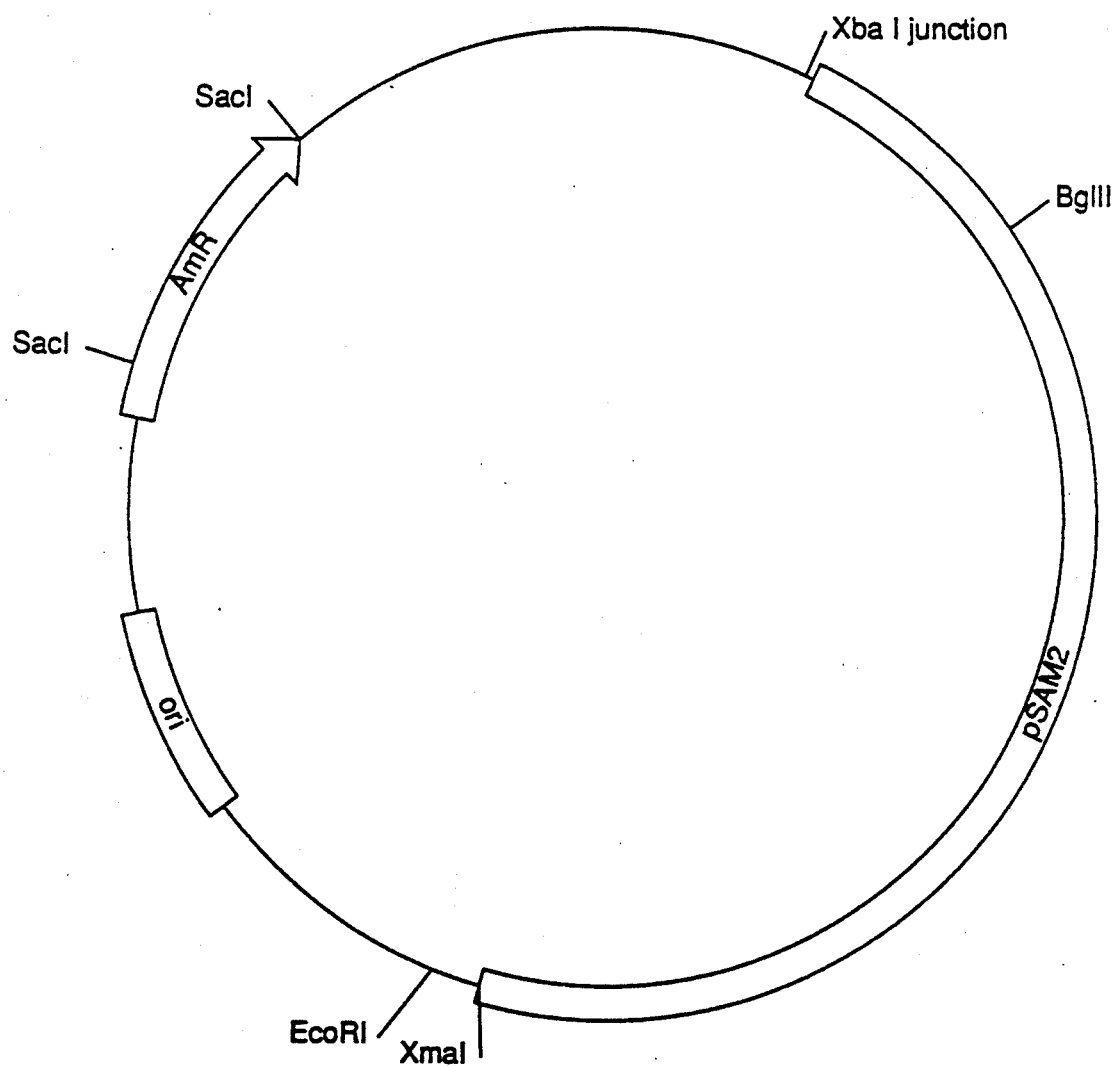
FIG. 4 is a restriction site and function map of plasmid pKC702.

FIG. 4 shows several typical responses in transduction frequency to increased phage concentration for species that are hosts for FP43 and for species that are not. While the efficiencies of transduction observed in different species of Streptomyces vary from about $10^{-8}$ to $10^{-4}$ per PFU, transduction efficiency has little bearing on the maximum number of transductants obtainable on a transduction plate. The highest transduction frequencies are obtained on nonrestricting or marginally restricting hosts that are susceptible to lysis by FP43.

In *Streptomyces griseofuscus*, a nonrestricting host on which the transducing lysates were prepared, the frequency of transductants increased linearly with increasing plaque-forming units between about $10^3$ and $10^5$ PFU per plate, then the frequency of transduction dropped due to lysis of potential transformants with further increases in P.F.U. However, insertion of pin in *S. griseofuscus* blocks lysis and permits efficient transduction at high m.o.i.

However, with *Streptomyces thermotolerans*, which is highly restricting for and does not support plaque formation of FP43, as many as $10^{10}$ PFU could be added per plate without lysing the transductants. With *S. thermotolerans* the frequency of transductants increased proportionally with increasing PFU up to about $10^8$ PFU per plate, then continued to rise at a slope of less than one up to nearly $10^{10}$ PFU per plate. Thus, there was no problem with lysis of transductants at high phage multiplicities. In this case, ~1500 transductants were observed from about $10^{10}$ PFU. Because the numbers of phage particles and cells added in the typical experiments are not serious limitations, very high multiplicities of phages and high cell densities can be used for highly restricting strains. These are clear advantages over protoplast systems where transformation is often most efficient at low protoplast concentrations, where uptake of plasmid is relatively inefficient, and where protoplast regeneration seldom approaches 100%.

FP43 forms plaques on *Streptomyces albus* P at an efficiency-of-plating (EOP) of about 10% relative to the maximum EOP observed on *S. griseofuscus*. The frequency of transductants of *S. albus* P increased linearly with increasing PFU to about $3 \times 10^7$ PFU per plate and then plateaued. However, the relative efficiency of transduction per PFU was about 100-fold lower than that observed on *S. griseofuscus*.

With *Streptomyces cirratus*, a strain that does not support plaque-formation by FP43, a very different response was observed. With *S. cirratus*, no transduction was observed at phage concentrations less than $10^8$ PFU per plate, but above this concentration the frequency of transductants increased proportionally with the square of phage concentration. As with *S. thermotolerans* there was no problem with lysis on the plate, but in fact there appeared to be a synergistic effect at high phage multiplicities.

This apparent bimolecular interaction suggests that transduction requires either two plasmids or one plasmid and one phage genome to establish plasmid replication. One possibility is that coinfection of plasmid and phage DNA reduces the effects of restriction. Perhaps the phage DNA initiates an abortive infection that competes out restriction endonuclease, thus allowing more efficient initiation of plasmid replication, although other possibilities could explain this interesting phenomenon. In any event, many transductants can be obtained at high phage multiplicity in a restricting background when bimolecular transduction kinetics are encountered.

The hft transduction system provides a variety of means for overcoming a host cell's endogenous DNA restriction/modification system. Elevated temperature can often inhibit secondary metabolic functions such as antibiotic production and sporulation in Streptomyces. Many restriction/modification systems may be regulated in a similar way, so growth of cells at elevated temperature might result in decreased expression of restriction and increased transduction in some restricting strains. To demonstrate this method of overcoming endogenous restriction systems, S. griseofuscus, S. albus P, S. phaeochromogenes, S. thermotolerans, and S. kentuckense were grown at 29° C. and 39° C. before transduction and incubated at 29°, 34° or 42° C. after transduction. Table 6 below details the results of this experiment.

TABLE 6

Effects of temperature on transduction of plasmid pRHB101 by FP43

| Strain | Temperature (°C.) Growth | Temperature (°C.) Transduction | Transduction frequency | $^a$Relative transduction |
|---|---|---|---|---|
| S. griseofuscus | 29 | 29 | $3.3 \times 10^{-4}$ | 1.1 |
| | 29 | 34 | $2.9 \times 10^{-4}$ | 1.0 |
| | 29 | 42 | $1.6 \times 10^{-4}$ | 0.55 |
| | 39 | 29 | $5.0 \times 10^{-5}$ | 0.17 |
| | 39 | 34 | $3.0 \times 10^{-5}$ | 0.10 |
| | 39 | 42 | $7.3 \times 10^{-5}$ | 0.25 |
| S. albus P | 29 | 29 | $6.2 \times 10^{-6}$ | 1.05 |
| | 29 | 34 | $5.9 \times 10^{-6}$ | 1.0 |
| | 29 | 42 | $2.7 \times 10^{-6}$ | 0.46 |
| | 39 | 29 | $4.3 \times 10^{-6}$ | 0.73 |
| | 39 | 34 | $4.3 \times 10^{-6}$ | 0.73 |
| | 39 | 42 | $3.9 \times 10^{-6}$ | 0.66 |
| S. phaeochromogenes | 29 | 29 | $5.0 \times 10^{-9}$ | 1.0 |
| | 29 | 34 | $5.0 \times 10^{-9}$ | 1.0 |
| | 29 | 42 | $<5.0 \times 10^{-9}$ | $<1.0$ |
| | 39 | 29 | $3.0 \times 10^{-8}$ | 6.0 |
| | 39 | 34 | $5.0 \times 10^{-8}$ | 10.0 |
| | 39 | 42 | $2.0 \times 10^{-8}$ | 4.0 |
| S. thermotolerans | 29 | 34 | $1.5 \times 10^{-8}$ | 1.0 |
| | 39 | 34 | $5.2 \times 10^{-6}$ | 350.0 |
| S. kentuckense | 29 | 34 | $4.7 \times 10^{-9}$ | 1.0 |
| | 39 | 34 | $2.2 \times 10^{-7}$ | 47.0 |

$^a$Transduction frequencies were normalized to those obtained when cells were grown at 29° C. and transductions were carried out at 34° C.

In the nonrestricting S. griseofuscus, transduction was decreased 5 to 10-fold relative to the 29° C. control by incubating cells at 39° C., whereas S. albus P showed very little variation in transduction frequencies with variation in temperature for cell growth or transduction. However, S. phaeochromogenes cells grown at 39° C. were 4 to 10-fold more transducible than cells grown at 29° C. These results suggest that the SphI restriction system functions poorly at elevated temperature. Maximum transduction was obtained when the cultures were grown at 39° C. and the transduction plates were incubated at 34° C. S. thermotolerans and S. kentuckense cells grown at 39° C. were 350-fold and 47-fold more transducible, respectively, than the corresponding cells grown at 29° C. Thus the temperature for cell growth can have a marked influence on efficiency of transduction in some species.

In any event, the data demonstrate that this transduction system can be readily manipulated by changing cell growth parameters to optimize transduction for particular species. This differs from the protoplast transformation systems that often have very inflexible requirements for cell growth before protoplast formation in order to obtain efficient regeneration of cells. For instance, growth of cells at elevated temperature can cause drastic inhibition of cell regeneration from protoplasts. Incorporation of pin further improves the transduction process in relatively non-restricting species such as S. griseofuscus.

The recombinant DNA cloning vectors of the present invention have broad utility and help fill the need for suitable cloning vehicles for use in Streptomyces and related organisms. Moreover, the ability of the present vectors to confer antibiotic resistance provides a functional means for selecting transductants. This is important because of the practical necessity for determining and selecting the particular cells that have acquired vector DNA in a transformation procedure.

Additional DNA segments that lack functional tests for their presence can also be inserted into the present vectors, and transductants containing the non-selectable DNA can be isolated by selection for thiostrepton resistance. Such non-selectable DNA segments can be inserted at any site, except within regions necessary for transduction or within the antibiotic resistance-conferring gene used for selection, and include, but are not limited to, genes that specify antibiotic modification enzymes and regulatory genes of all types.

The vectors comprising hft are also useful for ensuring that linked DNA segments are stably maintained in host cells over many generations. These genes or DNA fragments are maintained by exposing the transductants to selective pressure based upon the markers (i.e., an antibiotic resistance-conferring gene) present on the vector. Therefore, transductants that lose the vector cannot grow and are eliminated from the culture. Thus, the vectors of the present invention can stabilize and maintain DNA sequences of interest.

The cloning vectors and transductants of the hft system provide for the cloning of genes to improve yields of various products that are currently produced in Streptomyces and related cells. Examples of such products include, but are not limited to, streptomycin, tylosin, cephalosporins, actaplanin, narasin, monensin, tobramycin, erythromycin, and the like. The present invention also provides selectable vectors that are useful for cloning, characterizing, and reconstructing DNA sequences that code for commercially important proteins such as, for example, human insulin, human proinsulin, glucagon, interferon and the like; enzymatic functions in metabolic pathways leading to commercially important processes and compounds; or control elements that improve gene expression. These desired DNA sequences also include, but are not limited to, DNA that codes for enzymes that catalyze synthesis of derivatized antibiotics such as, for example, streptomycin, cephalosporin, tylosin, actaplanin, narasin, monensin and erythromycin derivatives, or for enzymes that mediate and increase bioproduction of antibiotics or other products. The capability for isolating and using such DNA segments allows for increasing the yield and availability of antibiotics that are produced by Streptomyces and related organisms.

Streptomyces can be cultured in a number of ways using any of several different media. Preferred carbohydrate sources in a culture medium include, for example, molasses, glucose, dextrin, and glycerol. Nitrogen sources include, for example, soy flour, amino acid mixtures, and peptones. Nutrient inorganic salts are also incorporated and include the customary salts capable of yielding sodium, potassium, ammonium, calcium, phosphate, chloride, sulfate, and like ions. As is necessary for the growth and development of other micro-organisms, essential trace elements are also added. Such trace elements are commonly supplied as impurities incidental to the addition of other constituents of the medium.

Streptomyces is grown under aerobic culture conditions over a relatively wide pH range of about 5 to 9 at temperatures ranging from about 15° to 40° C. For plasmid stability and maintenance, it is desirable to start with a culture medium at a pH of about 7.2 and maintain a culture temperature of about 30° C.

The following examples further illustrate and describe the invention disclosed herein. The invention is not limited in scope by reason of any of the following Examples; sources of reagents or equipment are provided merely for convenience and in no way limit the invention. Both an explanation of and the actual procedures for constructing the invention are described where appropriate.

EXAMPLE 1

Isolation of Phage FP43 from *Streptomyces griseofuscus* C581 (FP43)

A. List of Solutions

The following solutions are referred to throughout the Examples and are presented here for clarity.

| Ingredient | Amount |
| --- | --- |
| 1. P Medium (~100 ml): | |
| Sucrose | 10.3 g |
| $K_2SO_4$ | 0.025 g |
| Trace element solution (see #3) | 0.2 ml |
| $MgCl_2.6H_2O$ | 0.203 g |
| Water | 80 ml |
| After autoclaving add: | |
| $KH_2PO_4$ (0.5%) | 1 ml |
| $CaCl_2.2H_2O$ (3.68%) | 10 ml |
| (N-tris-(hydroxymethyl)-methyl-2-aminoethane sulphonic acid), "TES" buffer, 0.25 M, pH = 7.2 | 10 ml |
| 2. Trace element solution (~1 L): | |
| $ZnCl_2$ | 40 mg |
| $FeCl_3.6H_2O$ | 200 mg |
| $CuCl_2.2H_2O$ | 10 mg |
| $MnCl_2.4H_2O$ | 10 mg |
| $Na_2B_4O_7.10H_2O$ | 10 mg |
| $(NH_4)_6Mo_7O_{24}.4H_2O$ | 10 mg |
| $H_2O$ | 1 L |
| R2 Medium (~1 L): | |
| Sucrose | 103 g |
| $K_2SO_4$ | 0.25 g |
| Trace element solution | 0.25 g |
| $MgCl_2.6H_2O$ | 10.12 g |
| glucose | 10 g |
| L-asparagine.$1H_2O$ | 2.0 g |
| casamino acids | 0.1 g |
| Agar | 22 g |
| Water | to 700 ml |

The pH is adjusted to pH=7.2 before autoclaving. After autoclaving, add:

| Ingredient | Amount |
| --- | --- |
| $KH_2PO_4$ (0.05 g/100 ml) | 100 ml |
| $CaCl_2$ (2.22 g/100 ml) | 100 ml |
| TES Buffer (5.73 g/100 ml, pH = 7.2) | 100 ml |
| 4. Soft Nutrient Agar (SNA, ~1 L): | |
| Difco Nutrient Broth | 8 g |
| Agar | 5 g |

5. R2YE medium is R2 medium with 20 ml of 25% yeast extract added per liter.

6. Yeast Extract - Malt Extract (YEME, ~1 L):

| Ingredient | Amount |
| --- | --- |
| Yeast extract | 3 g |
| Peptone | 5 g |
| Malt extract | 3 g |
| Glucose | 10 g |

7. YEME+34% Sucrose Liquid Complete Medium is YEME with 340 g/L of sucrose.

| Ingredient | Amount |
| --- | --- |
| Yeast extract | 3 g |
| Malt extract | 3 g |
| Glucose | 2 g |
| Agar | 20 g |
| R2 Soft Agar | |
| Sucrose | 103 g |
| $K_2SO_4$ | 0.25 g |
| $MgCl_2$, 6 $H_2O$ | 10.12 g |
| Agar | 7 g |
| Water | to 800 ml |

The pH is adjusted to pH=7.2 before autoclaving. After autoclaving add:

| | |
| --- | --- |
| $CaCl_2$ 2.22 g/100 ml) | 100 ml |
| TES buffer (5.73 g/100 ml, pH 7.2) | 100 ml |

9. YMX Agar is 0.3% yeast extract, 0.3% malt extract, 0.2% dextrose, and 2.0% agar.

10. CSI Medium (~1 L):

| Ingredient | Amount |
| --- | --- |
| Soybean meal | 15 g |
| Casein | 1 g |
| Cerelose | 25 g |
| Blackstrap molasses | 3 g |
| $CaCO_3$ | 2.5 g |
| Czapek Mineral Stock | 2 ml |
| Water (deionized) | 1 L |
| pH adjusted to 7.2 prior to sterilization | |

11. Czapek's Mineral Mix (~1 L):

| | |
| --- | --- |
| KCl | 100 g |
| $MgSO_4.7H_2O$ | 100 g |
| Deionized Water | 900 ml |

$FeSO_4.7H_2O$ (2 g) was dissolved in 100 ml deionized water containing 2 ml of concentrated HCl. This solution was added to the above KCl/MgSO$_4$.7H$_2$O solution to complete preparation of the Czapek's Mineral Mix.

12. Bennett's Agar (~1 L):

| Ingredient | Amount |
| --- | --- |
| Deionized H$_2$O | 1000 ml |
| Potato Dextrin | 10 g |
| N-Z Amine A | 2 g |
| *Gibco bactoagar | 15 g |
| Gibco beef extract | 2 g |
| Yeast extract | 1 g |
| Czapek's mineral stock | 2 ml |

*Gibco Laboratories, 3175 Staley Road, Grand Island, N.Y. 14072

13. Nutrient Calcium Broth (NC broth) and Nutrient Calcium Agar (NCA)

NC broth contains 8 g of Difco (P.O. Box 1058, Detroit, Mich. 48232) nutrient broth per liter of deionized H$_2$O and is also 4 mM in Ca(NO$_3$)$_2$. NCA is NC broth containing 2% w/v agar.

14. TES Buffer

TES is an abbreviation for 2-{(tris-[hydroxymethyl]-methyl)amino}ethanesulfonic; to prepare TES buffer, a 1M solution of TES acid (125.6 g/500 ml) is mixed with an equal volume of 1M TES base and then diluted with distilled water to 0.25M in TES.

15. Sevag

Sevag is a 24:1 mixture of chloroform:isoamyl alcohol

16. φ Buffer

φ buffer is 10 mM TES and 10 mM Ca(NO$_3$)$_2$.

17. TE Buffer

TE buffer contains 10 mM Tris-HCl, pH=8, and 1 mM Na$_2$EDTA.

18. R2 Overlays (per 1 L)

| Ingredient | Amount |
| --- | --- |
| Sucrose | 103 g |
| MgCl$_2$ | 10.12 g |
| 0.151 M CaCl$_2$ | 100 ml |
| TES Buffer | 100 ml |
| Gibco Agar | 4.1 g |
| Distilled H$_2$O | to 1 L |

19. TSS Broth

TSS broth is prepared by adding 51.9 ml of 60% sucrose to 250 ml of trypticase soy broth (TSB). TSB is available from Baltimore Biological Laboratories (BBL), P.O. Box 243 Cockeysville, Md. 21031. As used herein, the TSS broth also contains enough glycine to give a final glycine concentration of 0.5%.

20. Tris is an abbreviation for Tris(hydroxymethyl) aminomethane. Tris buffers are well known in the art and are commercially available from Sigma Chemical Co., P.O. Box 14508, St. Louis, Mo. 63178.

21. NuSieve GTG agarose is a "low melting point" agarose which is commercially available from FMC Corp., Marine Colloids Division, Rockland, Me. 04841.

22. EDTA is an abbreviation for ethylenediaminetetraacetic acid. EDTA is available from the Sigma Chemical Co.

B. Procedures The procedures described below are well known to the skilled artisan. Details and references to procedures are provided merely to further convenience those who wish to practice the present invention.

(1) Centrifugation, unless otherwise specified in the examples, refers to a five minute centrifugation in an Eppendorf table-top centrifuge at room temperature. The centrifugal force generated therein is approximately 15,000 xg.

(2) Agarose gel electrophoresis is a technique well known in art. Agarose gel electrophoresis is described in great detail in T. Maniatis, E. Fritsch, and J. Sambrook, *Molecular Cloning-A Laboratory Manual* (1982), hereinafter Maniatis, at 150-171. Recovery of DNA bands from low melting point agarose such as NuSieve GTG is described in Maniatis at p. 170.

(3) Large scale isolation of plasmid DNA is described in Maniatis at pages 86-94. Plasmid purifications on cesium chloride-ethidium bromide gradients are described at pages 93-94.

(4) Cultivation of micro-organisms is well known in the art of microbiology. D. Hopwood, et al., *Genetic Manipulations of Streptomyces-A Laboratory Manual* (1985) is an excellent reference manual for all cultivation procedures and genetic engineering considerations.

B. Phage Isolation

Phage lysates and DNA were prepared in substantial accordance with the procedure described in Cox and Baltz, 1984, J. Bacteriol. 159: 499-504. A lyophilized culture of *Streptomyces griseofuscus* C581(FP43) is obtained from the Northern Regional Research Center (NRRL), Agricultural Research Service, Peoria, Ill. 61604 under the accession number NRRL 18184. The lyophilized culture is used to inoculate 10 ml of NC broth; the culture is then incubated at 29° C. in a gyratory incubator overnight (~16 hours). The culture is centrifuged to remove the cells and cellular debris; the supernatant is then passed through a 0.45µ filter, and the filtrate was saved and contained phage FP43 particles.

A lyophil of *Streptomyces griseofuscus* C581 is obtained from the American Type Culture Collection (ATCC), Rockville, Md. 20852 under the accession number ATCC 23916. The lyophilized culture is used to inoculate 10 ml of TSB broth (Baltimore Biological Laboratories, Inc. (BBL), P.O. Box 243, Cockeysville, Md. 21031) in a 50 ml flask. The culture is incubated at 29° C. in a gyratory incubator overnight.

Four 100 µl aliquots of the overnight culture of *Streptomyces griseofuscus* C581 are prepared and mixed, respectively, with 1.0 ml, 100 µl, 10 µl, and 1 µl of the lysate solution. The mixtures are then individually plated on NC agar (NC broth with 15 g/L agar) in 100×15 mm Petri plates and incubated at 34° C. overnight. The following morning, the plates are examined, and the plate showing nearly confluent lysis is used to prepare the phage FP43 stock solution. The FP43 stock solution is prepared by adding ~5 ml of NC broth to the plate showing nearly confluent lysis, incubating the plate at room temperature for one to two hours, and collecting the broth from the plate. The solution was centrifuged and the resulting supernatant passed through a 0.45µ filter to remove debris. The resulting phage FP43 solution typically contains 10$^8$ to 10$^{10}$ FP43 particles per ml—the exact titer is determined by plating several dilutions of the phage stock on a sensitive strain, such as *S. griseofuscus* C581.

C. Phage DNA Isolation

To prepare phage FP43 DNA, the procedure described in Example 1B was followed, except the lysates were prepared using four to six 9.5"×9.5" Petri dishes.

The plates were washed with 50 ml of NC broth to collect the phage particles. The lysates were centrifuged and the supernatants passed through a 0.45μ filter to remove cellular debris. The lysate was then centrifuged for 2 hours at 25° C. at 30,000 rpm to pellet the phage particles. Each pellet was resuspended in 1 ml of φ buffer; this solution was centrifuged in a tabletop centrifuge to pellet material that did not go back into solution. The supernatant was then layered on top of a CsCl gradient composed as follows (from most dense to least dense): 750 μl of 1.7 ρ CsCl in φ buffer; 750 μl of 1.6 ρ CsCl in φ buffer; 750 μl of 1.4 ρ CsCl in φ buffer; and ~2.45 ml of phage FP43 in φ buffer. The gradient was prepared in a polyallomer tube (½"×2"), which was placed in an SW50.1 rotor (Beckman Instruments, Inc., Spinco Division, P.O. Box 10200, Palo Alto, Calif. 94304). The solution was centrifuged at 25,000 rpm at 15° C. for 1 hour and yielded two bands: a brown-tinged top band and a blue-tinged lower band. The lower band was collected with a syringe and dialyzed against 2 to 3 liters of φ buffer overnight.

The dialyzed band was extracted for 30 minutes with 1.5 volumes of φ buffer-saturated phenol (25 ml phenol:10 ml φ buffer) and then re-extracted for 10 minutes with another 1.5 volumes of φ buffer-saturated phenol. The phage band was then extracted 3 times with one volume of Sevag. The phage DNA was precipitated with 0.1 volume of 3M sodium acetate (NaOAc), pH=8.0, and 1 volume of isopropanol. The precipitated phage FP43 DNA was spooled from the solution, washed with 70% ethanol and resuspended in ~1 ml of TE buffer, yielding a solution containing ~0.5 mg/ml of phage FP43 DNA.

EXAMPLE 2

Construction of Plasmid pRHB101

The isolation of pRHB101 was carried out in substantial accordance with the procedures of Birnbolm and Doly, 1979, Nucleic Acids Res. 7: 1513-1523 and Kieser, 1984, Plasmid 12: 19-36.

A. Isolation of Plasmid pIJ702

A lyophilized culture of Streptomyces lividans/pIJ702 (ATCC 39155) was used to inoculate 10 ml of TSS medium containing 25 μg/ml thiostrepton. The culture was incubated at 29° C. until the cells reach early stationary phase. The culture was then homogenized, and 5 ml of the homogenized culture were used to inoculate 100 ml of TSS also containing thiostrepton. The 100 ml of culture were incubated at 29° C. until the Streptomyces lividans/pIJ702 cells reached stationary phase.

The cells were collected and washed once with a 10.3% sucrose solution. The cells were then suspended in 24 ml of 20.3% sucrose, and 6 ml of 5X lysozyme solution (125 mM Tris-HCl, pH=8; 125 mM Na2EDTA, pH=8; 10 mg/ml lysozyme; and 10.3% sucrose) were added. The solution was mixed and then incubated at 30° C. for 30-60 minutes, and then, about 18 ml of a solution that was 0.3M NaOH, 1% SDS (sodium dodecyl sulfate), and prewarmed to 50° C. were added, mixed and the resulting mixture incubated at 80° C. for 10 minutes. The mixture was then cooled to room temperature, and 12 ml of a solution made by mixing 500 g phenol, 500 g CHCl$_3$, and 0.5 g 8-hydroxyquinoline in 200 ml H$_2$O were added and mixed well with the cell-extract. The phases were separated by centrifugation at 6000-8000 rpm for 10 minutes; approximately 45 ml of the resulting upper phase were transferred to a clean bottle.

Next, 4.5 ml of 3M NaOAc and 50 ml of isopropanol were added to the supernatant, and the solution was mixed and left at room temperature for 30 minutes. The solution was then centrifuged (8000 rpm for 30 minutes) and the resulting supernatant discarded. The pellet was resuspended in 7.5 ml TE buffer (10 mM Tris-HCl, pH=8, and 1 mM EDTA) containing 8 g of CsCl. About 0.5 ml of a 10 mg/ml solution of ethidium bromide was added to the solution, which was then centrifuged at 40,000 rpm for 48 hours at 20° C. The fraction containing the plasmid band was extracted 3-5 times with isopropanol saturated with TE buffer and CsCl to remove the ethidium bromide. After the extractions, the sample was diluted with four volumes of TE buffer, and then, two-and-one-half volumes of ethanol were added. The resulting solution was mixed and incubated overnight at −20° C.

The precipitate resulting from the overnight incubation at −20° C. was collected by centrifugation (10,000 rpm for 30 minutes), dried, and reprecipitated twice. The precipitations were done by suspending the pellet in TE buffer, adding NaOAc to 0.3M, adding 2.5 volumes ethanol, chilling at −70° C. for 10-15 minutes, and then centrifuging the solution as above. The procedure yielded about 100 μg of plasmid pIJ702 DNA, which was suspended in TE buffer at a concentration of 1 μg/μl and stored at 4° C. A restriction site and function map of plasmid pIJ702 is presented in FIG. 11 of the accompanying drawings.

About 3 μg (3 μl) of plasmid pIJ702 DNA were added to 5 μl of 10X SphI buffer (60 mM Tris-HCl, pH=7.4; 1.5M NaCl; 60 mM MgCl$_2$; 100 mM 2-mercaptoethanol; and 1 mg/ml bovine serum albumin (BSA)), 37 μl of H$_2$O, and 5 μl (~20 units; unit definitions herein correspond to those of New England Biolabs, 32 Tozer Road, Beverly, Mass. 01915-9990, unless otherwise indicated) of restriction enzyme SphI. The resulting reaction was incubated at 37° C. for one hour. About 5 μl of 10 X kinase buffer (0.1M MgCl$_2$; 50 mM dithiothreitol (DTT); and 0.5M Tris-HCl; pH=9.5), 10 μl of a 1:3 dilution (in kinase buffer) of calf-intestinal alkaline phosphatase (CAP, obtained from Boehringer-Mannheim Biochemicals, 7941 Castleway Drive, P.O. Box 50816, Indianapolis, Ind. 46250), and 35 μl of H$_2$O were added to the solution of SphI-digested plasmid pIJ702 DNA, and the solution was incubated at 38° C. for 30 minutes. The mixture was then placed at 65° C., and another 10 μl of a 1:3 dilution of CAP were added to the solution which was incubated at 65° C. for another 30 minutes. Yet another 10 μl of a 1:3 dilution of CAP was again added to the solution, which was incubated at 65° C. for another 30 minutes. Then, the SphI-digested, CAP-treated plasmid pIJ702 DNA was extracted twice with φ buffer-saturated phenol, extracted three times with ether, and collected by adjusting the sodium acetate (NaOAc) concentration of the reaction mixture to 0.30M, adding two volumes of ethanol, chilling the reaction mixture to −70° C., and centrifuging to pellet the precipitated DNA. The pellet was resuspended in 50 μl of TE buffer.

About 7.5 μg of phage FP43 DNA in ~20 μl of TE buffer were added to 5 μl of 10X SphI buffer, 20 μl of H$_2$O, and 5 μl (~20 units) of restriction enzyme SphI, and the resulting reaction was incubated at 37° C. for one hour. The SphI-digested phage FP43 DNA was extracted twice with φ buffer-saturated phenol, extracted three times with ether, precipitated, and resuspended in 50 μl of TE buffer.

The SphI-digested, alkaline phosphatase-treated plasmid pIJ702 DNA was added to the SphI-digested phage FP43 DNA, 37.5 μl of 10X ligase buffer (660 mM Tris-HCl, pH=8; 66 mM MgCl₂; 200 mM dithiothreitol; 10 mM ATP; and 50 μg/ml BSA), and 219 μl of H₂O. About 19 μl of T4 DNA ligase were added to the solution of DNA, and the resulting reaction was incubated at 15° C. overnight (~16 hours). The ligated DNA constituted the desired plasmid pRHB101 DNA. A restriction site and function map of plasmid pRHB101 is presented in FIG. 12 of the accompanying drawings. The ligated DNA, after precipitation and resuspension in 10 μl of TE buffer, was used to transform *Streptomyces lividans* TK23 as described in Example 4, below.

EXAMPLE 3

Isolation of Plasmid pRHB106

Plasmid pRHB106 was constructed in accordance with the foregoing procedure except that plasmid pMT660 was used instead of plasmid pIJ702. However, for convenience, plasmid pRHB106 can also be obtained in *Streptomyces griseofuscus* C581 from the NRRL under the accession number NRRL 18183.

Plasmid pRHB106 need not be isolated from a phage FP43 genomic library as is described for plasmid pRHB101 in Examples 2 and 4. Instead, *S. griseofuscus* C581/pRHB106 can be used to prepare a transducing lysate as described in Example 4. The transducing lysate will contain phage particles that have packaged plasmid pRHB106 DNA and can be used in transductions as described in Example 5.

EXAMPLE 4

Identification of Plasmid pRHB106 Illustrating the Isolation of an FP43 hft Sequence-Containing Vector The procedure set forth below can be used to identify any hft-containing FP43 restriction fragment. In Example 2, a genomic library of phage FP43 was constructed, which included the hft-containing plasmid pRHB101. The procedure set forth below demonstrates how plasmid pRHB101 was isolated from the genomic library. Briefly stated, the procedure first involves protoplast transformation of *Streptomyces lividans* TK23. These transformants, identified on the basis of their mel⁻, tsrR phenotype, were examined for size of insert (FP43) DNA. A group of plasmids, each containing a different SphI restriction fragment and constituting a genomic library of phage FP43, were isolated and used to transform *S. griseofuscus*. The *S. griseofuscus* transformants were infected with phage FP43 to prepare lysates. The lysates were examined for their ability to transduce *S. griseofuscus*. The lysate that yielded the highest transduction frequency comprised plasmid pRHB101 packaged into phage particles.

A. Transformation of *Streptomyces lividans*

*Streptomyces lividans* TK23 (NRRL 15826) was grown in a 10 ml culture for 40–48 hours at 30° C. in TSB broth. The culture was then homogenized and sonicated, and the mycelial fragments were recovered by centrifugation (800Xg for 10 minutes in a bench top centrifuge) and washed once with 10 ml of P media. The mycelial fragments were resuspended in 10 ml of P media containing 5 to 10 mg/ml of egg-white lysozyme (Cal-biochem-Behring, P.O. Box 12087, San Diego, Calif. 92112) and incubated for 1 hour at 4° C. During this interval the suspension was pipetted up and down once or twice to disperse clumps. The protoplasts were recovered by centrifugation (800Xg for 10 minutes) and washed twice with 10 ml of P medium. The protoplasts were then suspended in 10 ml of P medium.

About 200 μl of protoplasts and about 0.3 to 0.5 μg of the ligated DNA prepared in Example 2 were added together per transformation. About 0.5 ml of 20% PEG 1000 in P medium was then added to the protoplast-DNA mixture. The mixture was pipetted up and down once or twice to mix the contents. At this point, the suspension was plated. The cells were plated onto R2 plates using about 3 to 4 ml of R2 overlay per plate. The R2 medium was supplemented with 150 μg/ml tyrosine for identification of mel⁺ and mel⁻ transformants. The regeneration plates contained about 100 μl of the protoplast-DNA-PEG 1000 solution per plate.

The plates were incubated at 30° C. overnight; the following day, the plates were overlayed with R2 overlays containing enough thiostrepton to give a final concentration of 25 μg/ml after diffusion. Incubation at 30° C. was continued; those transformants possessing an intact tyrosinase (mel) gene became black after growth in the presence of tyrosine.

Thiostrepton-resistant, white transformants were isolated, and a number of single colonies were used to inoculate 10 ml TSB cultures containing thiostrepton (25 μg/ml). The cultures were homogenized and then grown overnight at 30° C. in a rotary shaker.

Plasmid isolation for analysis was in accordance with the procedures described in Example 2A; the CsCl gradients of Example 2A were replaced by ethanol precipitations. The mycelium was collected by centrifugation, washed twice with 10.3% sucrose, and then suspended in 1–2 ml of 10.3% sucrose. Four hundred μl of the cell mixture were transferred to a small tube, and 100 μl of lysozyme solution were added. The suspension was incubated at 30° C. for 30–60 minutes, followed by the addition and mixing of 300 μl of 0.3M NaOH containing 1% SDS. The latter solution was kept at 50° C. before its addition to the cell mix. The cell mixture was placed at 80° C. for 10 minutes, cooled to room temperature, and then extracted with 200 μl of phenol:CHCl₃ (50:50). The aqueous phase was transferred to a clean tube, made 0.3M in NaOAc, and then one volume of isopropanol was added. The DNA was incubated at room temperature for five minutes and then pelleted by centrifugation. The pellet was dissolved in 400 μl of TE buffer and made 0.3M in NaOAc. About 2.5 volumes of ethanol were added, and the mixture was incubated at −70° C. for 30 minutes. After centrifugation and another precipitation, the plasmid DNA was suspended in 50 μl of TE buffer. Restriction enzyme cutting and electrophoretic analysis of the reaction products were used to determine plasmid structure. A variety of different plasmids, each containing a different SphI restriction fragment of phage FP43 were isolated by this procedure.

B. Transformation of *Streptomyces griseofuscus* C581 (ATCC 23916)

The plasmids isolated in Example 4A were used to transform *Streptomyces griseofuscus* C581. A 10 ml overnight culture of *S. griseofuscus* was prepared as described for *S. lividans* in Example 4A. The culture was collected by centrifugation, washed with 10 ml of P medium, and resuspended in 10 ml of P medium containing 5 to 10 mg/ml of lysozyme. The cells were then incubated at 4° C. for one hour, collected by centrifugation, washed twice with 10 ml of P medium, and resuspended in 3 ml of P medium. For each plasmid prepared in Example 4A (about 0.5 μg in 10 μl of TE buffer), about 150 μl of protoplasts were added to the solution of plasmid DNA. Then, about 100 pl of 55% PEG 1000 and 1 ml of P media were added to each protoplast-DNA mixture. The cells were plated and overlayed with thiostrepton as described in Example 4A.

C. Preparation of Lysates and Transduction

For each plasmid, several transformants obtained in Example 4B were used to prepare lysates using phage FP43 as described in Example 1. These lysates were then used to transduce *Streptomyces griseofuscus* C581. Transduction was carried out by first obtaining an overnight culture of *S. griseofuscus* C581, homogenizing and sonicating that culture, and removing several 100 μl aliquots. To each aliquot was added 100 μl of one of the lysates, both directly and after serial dilution, and the mixture was plated on R2 agar using R2 overlays. Thiostrepton was added via an overlay at least 6 hours after plating. The lysate that yielded the greatest number of thiostrepton-resistant transductants contained plasmid pRHB101 packaged into infective FP43 phage particles.

EXAMPLE 5

A. Culture of *E. coli* K12 DH5α/pKC684

A lyophil of *E. coli* DH5α/pKC684 can be obtained from the Northern Regional Research Laboratories (NRRL), Peoria, Ill. 61604, under the accession number B-18541 and used directly in the process described below.

One liter of TY broth (10 g tryptone, 5 g NaCl, and 5 g yeast extract per liter) containing 100 μg/ml apramycin is inoculated with a culture of *E. coli* DH5α/pKC684 and incubated with aeration at 37° C. overnight (15-18 hours). The resulting culture is used as a source of plasmid pKC684.

B. Isolation of Plasmid pKC684

The culture prepared in Example 5A is centrifuged at 8000 rpm using a GSA rotor for 10 minutes at 4° C. to pellet the cells. The resulting supernatant is discarded. The cell pellet is resuspended in 28 ml of a solution 25% w/v sucrose and 50 mM Tris-HCl, pH=8.0. The following are added to the resuspended cells: 1 ml of 5 mg/ml lysozyme (freshly prepared in the resuspension solution); 1.6 ml of 0.5M EDTA (pH 8), and 0.2 ml of 5 mg/ml RNase A. The resulting mixture is incubated on ice for 15 minutes. Three ml of lysing solution (50 mM Tris-HCl, pH=8.0, 3% Triton X-100 w/v, and 200 mM EDTA) are added to the lysozyme-treated cells with gentle mixing. The resulting solution is incubated on ice for another 15 minutes.

The cellular debris is removed from the solution by centrifugation at 20,000 rpm for about 45 minutes at 4° C. About 28.6 g of CsCl and ~1 ml of a 5 mg/ml ethidium bromide solution are added to the ~30 ml of supernatant. Then, the volume is adjusted to 40 ml with water and the solution decanted into an ultracentrifuge tube. The tube is sealed, and the solution is centrifuged at 49,000 rpm for ~18 hours. The resulting plasmid band, visualized with ultraviolet light, is isolated, extracted with 4 to 5 treatments with isobutanol to remove the ethidium bromide, and dialysed against three changes of ~20 volumes of TE buffer (10 mM Tris-HCl, pH=7.5, and 1 mM EDTA). The dialysate is collected and then extracted with 2 treatments of equal volumes of phenol (equilibrated with TE) ~pH 8 followed by 2 equal volume Sevag extractions. Three volumes of ethanol and 0.1 volumes of 3M sodium acetate solution are added to the aqueous extractions and the plasmid DNA is pelleted by centrifugation at 10,000 rpm using a Sorvall HB4 rotor at −4° C. The resulting DNA pellet is rinsed first with 70% ethanol and then with 100% ethanol and dried under vacuum.

The ~1.0 mg of plasmid pKC684 DNA obtained by this procedure is suspended in 1.5 ml of TE buffer and stored at 4° C. A restriction site and function map of plasmid pKC684 is presented in FIG. 2 of the accompanying drawings.

EXAMPLE 6

Plasmid pKC685

Figure 3:
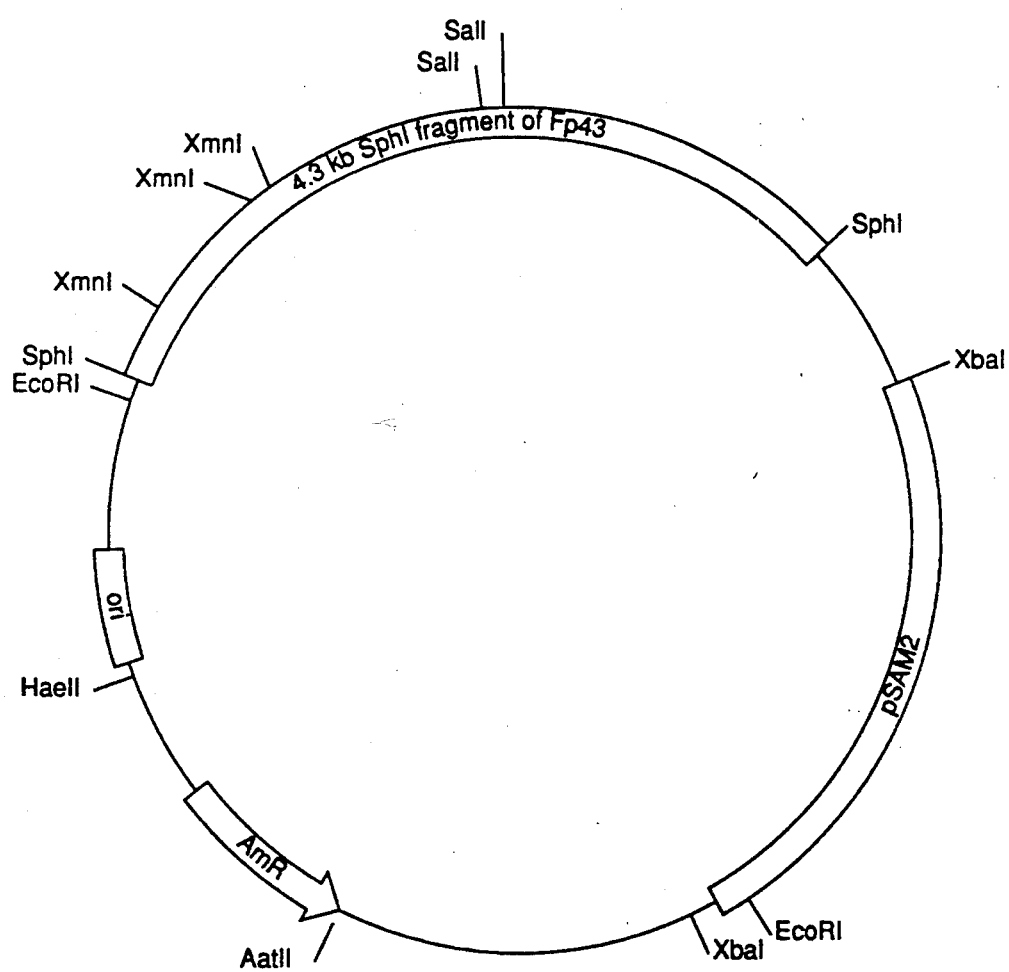
FIG. 3 is a restriction site and function map of plasmid pKC685.

Plasmids pKC684 and pKC685 differ only in the orientation of the ~2.9 kb EcoRI fragment. A restriction site and function map of plasmid pKC685 is provided in FIG. 3. Plasmid pKC685 can be prepared by digesting the plasmid pKC684 obtained in Example 5 with the restriction endonuclease EcoRI and ligating the phenol-extracted digestion mixture.

Construction of Plasmid pKC685

Three μg of plasmid pKC684 are digested at 37° C. with ~10 U of EcoRI (New England Biolabs) in a digestion mixture comprising: 100 mM NaCL, 100 mM Tris-HCl (pH=7.5), 5 mM MgCl$_2$, 100 μg/ml bovine serum albumin, and 10 mM dithiothreitol (DTT).

The EcoRI digest of plasmid pKC684 is then ethanol precipitated, washed, and vacuum dried. The digestion components are then ligated using ~10 U T4 DNA ligase (New England Biolabs) in a final volume of 20 μl. The ligation buffer consisted of 50 mM Tris-HCl (pH=7.8), 10 mM MgCl$_2$, 20 mM DTT, 1 mM ATP and 50 μg/ml bovine serum albumin. The ligation proceeds at ~16° C. for about 18 hours.

(B) *E. coli* Transformation Protocol

The transformation protocol provided below was used in all aspects of the invention which involved *E. coli* transformation. The ligation mixture was transformed into *E. coli* DH5α as follows. Preferably, the competent *E. coli* DH5α were purchased from Bethesda Research Lab, Gaithersburg, Md. 20877. Alternatively, competent *E. coli* DH5α can be prepared in substantial accordance with the method of Maniatis, p. 252-253. 2.5 μl of the ligation mixture was added to 100 μl of competent *E. coli* DH5α containing ~10$^8$ cells/ml. The transformation mixture was incubated on ice for approximately 30 minutes. The temperature was then raised by immersing the tube in a water bath at 42° C. to heat shock the cells for approximately 1 minute. Cells were allowed to grow 2 hours in ~1 ml TY broth at 37° C. on a roller drum then selected by plating the transformation mixture on TY agar with apramycin (100 μg/ml).

Apramycin resistant (AmR) colonies were then screened to determine which transformants comprise the plasmid pKC685. Plasmids were harvested from the transformed cells as follows.

(C) Plasmid Preparation

Transformed *E. coli* DH5α were cultured overnight in 5 ml TY broth. 4 ml of the broth were then harvested for restriction analysis. Cells were pelleted by centrifugation. The cell-pellet was resuspended to a volume of approximately 500 μl in 25 mM Tris-HCl (pH=8) with 25 mM EDTA. 250 μl of 0.2N NaOH with 2% w/v SDS was added and the mixture was vortexed. 1.5 ml Eppendorf snap-top tubes are preferred containers for the plasmid preparations and all centrifugation steps were performed using a table-top Eppendorf centrifuge. The tubes were warmed to 70° C. for ten minutes, then cooled to room temperature. 100 μl of phenol:-chloroform (1:1) was added and the mixture was vortexed. The mixture was centrifuged ~3-5 minutes in a table-top Eppendorf centrifuge. The aqueous phase was aspirated and removed to a fresh 1.5 ml Eppendorf tube. 70 μl of 3M sodium acetate was added, then the tube was filled with isopropanol. After a 5-10 minute centrifugation, the supernatant was decanted and the tube was centrifuged another 5 to 10 minutes. The remaining droplets were aspirated, leaving only the precipitated DNA in the tube. The DNA pellet was dissolved in 500 μl TE and 25 μl of 100 mM spermine was added. Centrifugation for 5 minutes at room temperature precipitated the DNA. The supernatant was decanted and the DNA pellet was then washed with Keiser wash solution, which comprises 300 μl of 0.3M sodium acetate with 100 mM $MgCl_2$ and 700 μl ethanol. After mixing the DNA and the Keiser wash solution, the DNA was centrifuged at room temperature for 5 minutes. The DNA pellet was then washed with ethanol, dried under vacuum, and resuspended in 10-20 μl of TE.

(D) Restriction Endonuclease Mapping

Plasmid DNA isolated above was then analyzed for the orientation of the EcoRI insert to distinguish which transformants comprise pKC685, pKC684, or plasmids which had deleted ~7.1 kb FP43 and pSAM2 fragment. ~3 μg of plasmid DNA was digested with ~10 U of Xba I for 1 hour at 37° C. in 20 μl digestion buffer comprising 50 mM NaCl, 10 mM Tris-HCl (pH=7.9), 10 mM $MgCl_2$, 10 mM DTT and 100 μg/ml bovine serum albumin. Digestion of plasmid pKC684 with Xba I produced ~7.2 kb and ~2.8 kb fragments. Digestion of plasmid pKC685 with Xba I produced ~5.5 kb and ~4.6 kb fragments. Xba I digestion of the deletion plasmid resulted in a single band of ~2.9 kb.

EXAMPLE 7

A. Construction of Plasmid pKC702

Plasmid pKC702 was derived from plasmid pKC684 by excision of the ~4.3 kb FP43 derived fragment. Approximately 3 μg of plasmid pKC684 were digested with 12 U Xmn I and 40 U Xba I in a 20 μl digestion buffer comprising: 50 mM NaCl, 10 mM Tris-HCl (pH=7.9), 10 mM $MgCl_2$, 10 mM DTT and 10 μg/ml bovine serum albumin for 1 hour at 37° C. The pKC684 digest was then electrophoresed through 1% NuSieve GTG agarose in TAE (40 mM Tris-acetate, 1 mM EDTA pH 8.0). The 5.5 kb pKC684 fragment was excised by removing the band in an ~40 μl gel plug. The gel plug containing the ~5.5 kb band of pKC684 was then heated to 70° C. for 10 minutes.

10 μl of the melted plug was added to a prewarmed, 37° C. solution, comprising 2 μl 0.2M DTT, 2 μl 10X ligase buffer (500 mM Tris-HCl pH 7.8 100 mM $MgCl_2$), 2 μl 10 mM ATP, 2 μl $H_2O$, and 2 μl T4 DNA ligase (New England Biolabs). Ligation proceeded at 15° C. overnight and resulted in plasmid pKC702. A restriction site and function map of pKC702 is provided in FIG. 4.

B. Transformation of Competent *E. Coli*

The ligation mixture comprising plasmid pKC702 was used to transform competent *E. coli* DH5α in substantial accordance with Example 6B. 2.5 μl of the ligation mixture was warmed at 70° C. for 5 minutes, then added to 100 μl of competent *E. coli* DH5α. The transformation mixture was then incubated on ice for approximately 30 minutes. The cells were then heat shocked by a one minute incubation at 42° C. Cells were grown for 2 hours in ~1 ml TY broth at 37° C. on a roller drum then selected by plating the transformation mixture on TY agar (TY broth containing 2% w/v agar) containing 100 μl/ml apramycin.

Apramycin resistant clones were then screened to determine which transformants comprise plasmid pKC702. Screening was accomplished as follows. The transformants were cultured overnight at 37° C. in separate tubes containing 5 ml of TY broth with apramycin (100 μg/ml).

Plasmids were harvested and prepared for restriction nuclease mapping in substantial accordance with the teachings of Example 6C. Restriction endonuclease mapping was used to confirm the structure of pKC702. 3 separate 1 μl samples were digested as follows. One 1 μl sample was digested with 10 U Bgl II (New England Biolabs) in a total volume of 20 μl in a digestion buffer consisting of 50 mM NaCl, 10 mM Tris-HCl (pH=7.4), 10 mM $MgCl_2$, 10 mM DTT and 10 μl/ml bovine serum albumin (Bgl II digestion buffer), for 1 hour at 37° C. A second 1 μl sample of plasmid DNA was digested with 20 U of Hind III (New England Biolabs) for 1 hour at 37° C. in a total volume of 20 μl and in a digestion buffer consisting of 50 mM NaCl, 50 mM Tris-HCl (pH=8.0), 10 mM $MgCl_2$, 10 mM DTT and 100 μg bovine serum albumin (Hind III digestion buffer). A third 1 μl sample of plasmid DNA was digested with both Bgl II and Hind III in substantial accordance with the conditions set forth above. Gel electrophoresis of the digests and comparison of the fragment sizes to the restriction map of pKC702 are determinative of which transformants comprise plasmid pKC702.

EXAMPLE 8

Construction of Plasmid pKC703

Plasmid pKC703 was prepared from plasmid pKC685 as follows. Plasmid pKC685 was prepared by culturing *E. coli* DH5α/pKC685 and isolating plasmid DNA in substantial accordance with the method of Example 5. 3 μl of plasmid pKC685 was digested with 20 U of Xba I (New England Biolabs) for 1 hour at 37° C. in a 20 μl total volume of a digestion buffer comprising: 50 mM NaCl, 10 mM Tris-HCl (pH=7.9), 10 mM DTT, 10 mM $MgCl_2$, and 100 μg/ml bovine serum albumin (Xba I digestion buffer).

Figure 5:
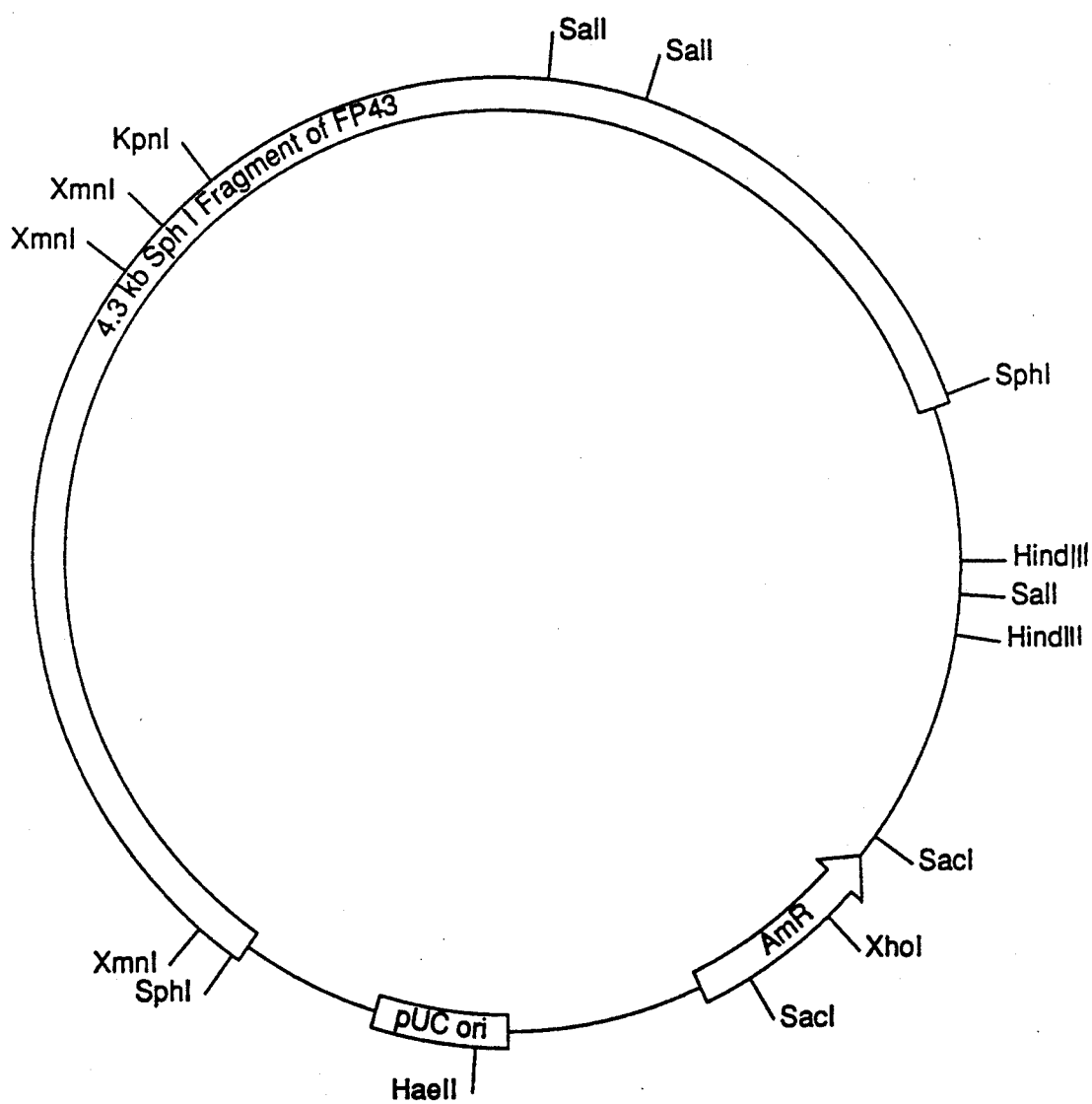
FIG. 5 is a restriction site and function map of plasmid pKC703.

The Xba I digest of plasmid pKC685 was then separated by electrophoresis using 1% NuSieve GTG agarose in TAE buffer. The ~7.5 kb Xba I restriction fragment was harvested from the gel by removing the ~7.5 kb band in an ~40 μl plug. The gel plug containing the ~7.5 kb fragment was then melted and the ~7.5 kb fragment was ligated in substantial accord with the method of Example 6. Ligation of the ~7.5 kb Xba I fragment resulted in plasmid pKC703. A restriction site and function map of plasmid pKC703 is provided in FIG. 5.

2.5 μl of the ligation mixture comprising plasmid pKC703 was used to transform competent *E. coli* DH5α (BRL) in substantial accordance with the teaching of Example 7. Transformants were selected for apramycin resistance by plating the transformation mixture on TY agar containing apramycin (100 μg/ml). Isolated colonies were then screened for the presence of plasmid pKC703 as follows.

Transformed *E. coli* DH5α was cultured overnight in 5 ml TY broth. 4 ml of the broth was harvested for restriction analysis. Cells were pelleted by centrifugation. The cell pellet was resuspended to a volume of approximately 500 μl in 25 mM Tris-HCl (pH=8) with 25 mM EDTA. 250 μl of 0.2N NaOH with 2% w/v SDS was added and the mixture vortexed. The tubes were warmed to 70° C. for ten minutes, then cooled to room temperature. 100 μl of phenol:chloroform (1:1) was added and the mixture was vortexed. The mixture was centrifuged ~3–5 minutes in a table-top Eppendorf centrifuge. The aqueous phase was harvested and removed to a fresh 1.5 ml Eppendorf tube. 70 μl of 3M sodium acetate was added, then the tube was filled with isopropanol. Following a 5–10 minute centrifugation, the supernatant was decanted and the tube was centrifuged another 5 to 10 minutes. The remaining droplets were aspirated, leaving only the precipitated DNA in the tube. The DNA pellet was dissolved in 500 μl TE and 25 μl of 100 mM spermine was then added. Centrifugation for 5 minutes at room temperature precipitated the DNA. The supernatant was decanted. The DNA pellet was then washed with Keiser wash solution. After mixing the DNA and the Keiser wash solution, the DNA was centrifuged at room temperature for 15 minutes. The DNA pellet was then washed with ethanol, dried under vacuum, and resuspended in 10–20 μl of TE.

The plasmid DNA prepared above was then mapped with the restriction endonucleases Bgl II, Hind III, and Xmn I. 1 μl of the plasmid preparation was digested with 8 U Bgl II (New England Biolabs) at 37° C. for 1 hour in a total 20 μl digestion volume comprising 100 mM NaCl, 10 mM Tris-HCl (pH=7.4), 10 mM MgCl₂, 10 mM DTT, and 100 μg/ml bovine serum albumin (Bgl II digestion buffer). A second 1 μl sample of the plasmid preparation was digested with 20 U Hind III (New England Biolabs) for 1 hour at 37° C. in a total digestion volume of 20 μl comprising 50 mM NaCl, 50 mM Tris-HCl (pH=8.0), 10 mM MgCl₂, and 10 U μg/ml bovine serum albumin (Hind III digestion buffer). A third 1 μl plasmid preparation sample was digested with 10 U of Xmn I (New England Biolabs) for 1 hour at 37° C. in a 20 μl total digestion volume comprising 50 mM NaCl, 10 mM Tris-HCl (pH=8.0), 10 mM MgCl₂, 10 mM dithiothreitol, and 100 μg/ml bovine serum albumin (Xmn I digestion buffer). Plasmid pKC703 was not cut by Bgl II, yielded a ~7.5 kb fragment when digested with Hind III, and yielded fragments of ~5.5 kb, ~1.7 kb, and ~200 base pairs when digested with Xmn I.

EXAMPLE 9

Construction of Plasmid pKC721

Figure 6:
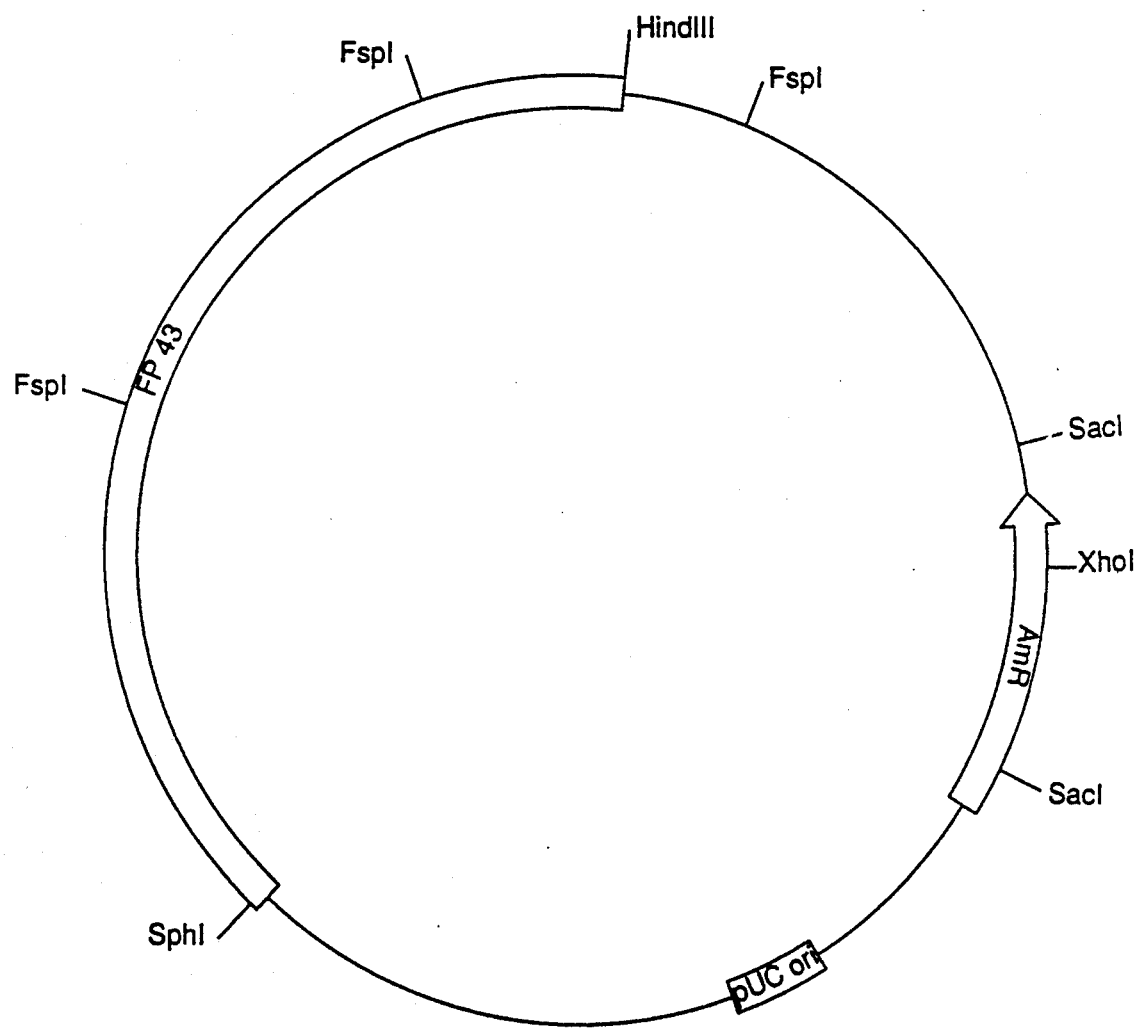
FIG. 6 is a restriction site and function map of plasmid pKC721.

Plasmid pKC721 was constructed by deleting the ~2 kb Sal I fragment from plasmid pKC703. A restriction site and function map of plasmid pKC721 is provided in FIG. 6.

Plasmid pKC703 DNA was prepared as taught in Example 8. 3 μg of plasmid pKC703 was digested with 30 U of Sal I (New England Biolabs) in a 20 μl total digestion volume comprising 150 mM NaCl, 10 mM Tris-HCl (pH=7.9), 10 mM MgCl₂, 10 mM DTT, and 100 μg/ml bovine serum albumin (Sal I digestion buffer). The digestion mixture was then electrophoresed on a 1% NuSieve GTG agarose gel and the ~5.5 kb band removed therefrom in a 40 μl plug. The gel plug containing the ~5.5 kb Sal I fragment was melted and the DNA therein ligated in substantial accordance with the teachings of Example 7. Plasmid pKC721 results from the ligation of the ~5.5 kb fragment (see FIG. 6).

EXAMPLE 10

Transformation of Streptomyces Griseofuscus and DNA Isolation Therefrom

A. Preparation of Protoplasts

The method set forth below was used in all experiments wherein transformation of *Streptomyces griseofuscus* was required.

A lyophil of *Streptomyces griseofuscus* C581 is obtained from the American Type Culture Collection (ATCC), Rockville, Md. 20852 under the accession number ATCC 23916. The lyophilized culture is used to inoculate 10 ml of TSB broth in a 50 ml flask. The culture is incubated at 29° C. in a gyratory incubator overnight.

One half ml of a fully grown overnight culture of Streptomyces, homogenized, was used to inoculate 9.5 mls of TSB plus 0.5% glycine. The culture was incubated at 30° C. for 24 hours. After homogenization with a tissue grinder, 0.5 ml of homogenate was used to inoculate 9.5 ml of fresh TSB supplemented with 0.5% glycine. The culture was incubated at 30° C. for 24 hours. The culture was homogenized and transferred to a 50 ml sterile polystyrene centrifuge tube. The cells were pelleted by centrifugation, washed with 10 ml of P medium and resuspended in 10 ml of P medium with 1 mg/ml lysozyme, then incubated at room temperature for 15–30 minutes. Protoplast formation was monitored by examining small samples under a phase-contrast microscope. Protoplasts are spherical.

B. Protoplast Transformation

The protoplasts were centrifuged as before and washed once in P medium. The cells were resuspended in 10 ml of P medium and 150 μl of protoplasts for each transformation were placed in a 1.5 ml Eppendorf tube. Up to 10 μl of plasmid DNA in TE buffer were added with gentle mixing. One hundred μl of 50% polyethylene glycol 1000 in P medium were added immediately, mixed well and allowed to sit at room temperature 30 seconds.

The transformation mixture was then plated on R2YE agar using an overlay of R2 soft agar containing a 25 μg/ml final concentration of apramycin. The plates were incubated at 30° C. and transformants appeared 2–3 days later.

Individual colonies of transformants were cultured in 10 ml TSB containing apramycin (25 μg/ml) 2–3 days at 30° C.

C. Preparation of Total DNA

The following procedure was used to prepare total DNA from Streptomyces and thus supports several other examples. The culture was homogenized and aliquoted into 1.5 ml Eppendorf tubes. The tubes were centrifuged and the supernatants were removed. The pellets were resuspended in ~0.5 ml of medium containing 0.3M sucrose, 25 mM Tris (pH=8.0), 25 mM EDTA, 5 mg/ml lysozyme, and 50 μg/ml RNase A. Following a 30 minute incubation at 37° C., 250 μl of 2% sodium dodecyl sulfate was added and the mixture was vortexed for ~1 minute. 250 μl of neutral phenol:chloroform (phenol:chloroform 1:1 equilibrated vs. 0.1M Tris-HCl, pH 8.0) was added. (Equilibration refers to adding 0.1M Tris-HCl pH 8.0 until a biphasic solution forms.) The tube and its contents were vortexed for ~30 seconds. The aqueous phase was aspirated using a Pasteur pipette. The phenol/chloroform extraction was repeated four times at which point the interface was clear. A 0.1 volume of 3M sodium acetate was added. 1 volume of isopropanol was then added, and the contents were mixed and held at room temperature for 5 minutes. The tubes were then centrifuged in an Eppendorf table-top centrifuge for 5 minutes. After centrifugation, the upper phase was aspirated. After an additional 1 minute centrifugation the remaining liquid was aspirated, leaving only the pellet. The pellet was dissolved in 500 μl of TE. 25 μl of 0.1M spermine was added and the tubes were mixed at room temperature for 5 minutes. Centrifugation at room temperature for 10 minutes resulted in precipitation of the DNA. After aspiration of the supernatant the pellet was resuspended in 300 μl final volume comprising 1 mM MgCl₂ and 0.3M sodium acetate. 700 μl of ethanol were added, the contents were mixed and then centrifuged at room temperature for 5 minutes. The supernatant was decanted, after which the DNA pellet was washed with ethanol and dried under vacuum. The DNA pellet was then resuspended in 50 μl TE.

D. Preparation of Streptomyces Plasmids

The method of Streptomyces plasmid preparation set forth below was used to prepare plasmid DNA from all Streptomyces transformants utilized in the present examples.

Approximately 5 ml of an overnight broth homogenate was centrifugally harvested. The cell pellet was resuspended to a final volume of 2 ml in STE (15% sucrose, 50 mM Tris-HCl [pH 8.0], 50 mM EDTA [pH 8.0]) containing approximately 0.3 mg lysozyme. The suspension was mixed and then incubated at 37° C. for 1 hour. Four aliquots of 500 μl each were placed in separate 1.5 ml Eppendorf tubes.

250 μl of 0.3M NaOH containing 2% SDS was added to each tube. The tubes were vigorously vortexed, then heated at 70° C. for 15 minutes. The tubes were allowed to cool to room temperature. Eighty μl of 1:1 phenol:chloroform were added. The tubes were vigorously vortexed, then centrifuged for 5 minutes. The aqueous phase containing the plasmid DNA was then harvested from each tube and placed in a fresh 1.5 ml Eppendorf tube. 70 μl of 3M sodium acetate and 700 μl of isopropanol were added to each tube. The tubes were mixed well, then centrifuged for 10 minutes. The supernatant was aspirated leaving only the pelleted DNA. The tube was centrifuged 1 minute longer and aspirated again to remove all isopropanol. Plasmid DNA was resuspended in 500 μl TE and 25 μl 0.1M spermine. The contents were mixed then centrifuged for 10 minutes. The supernatant was discarded. The pellet was then washed in Keiser wash solution. After a 10 minute centrifugation, the supernatant was discarded and the pellet was washed with ethanol and then dried under vacuum. The contents of all four tubes were pooled and resuspended in a total volume of 10 μl TE.

EXAMPLE 11

Transformation of *Streptomyces griseofuscus* with Plasmid pKC721

Plasmid pKC721 was constructed in Example 9. Transformation procedures were carried out in substantial accordance with the teachings of Example 10. Transformants were selected on R2YE containing apramycin (25 μg/ml).

EXAMPLE 12

Construction of Plasmid pKC 761

Figure 7:
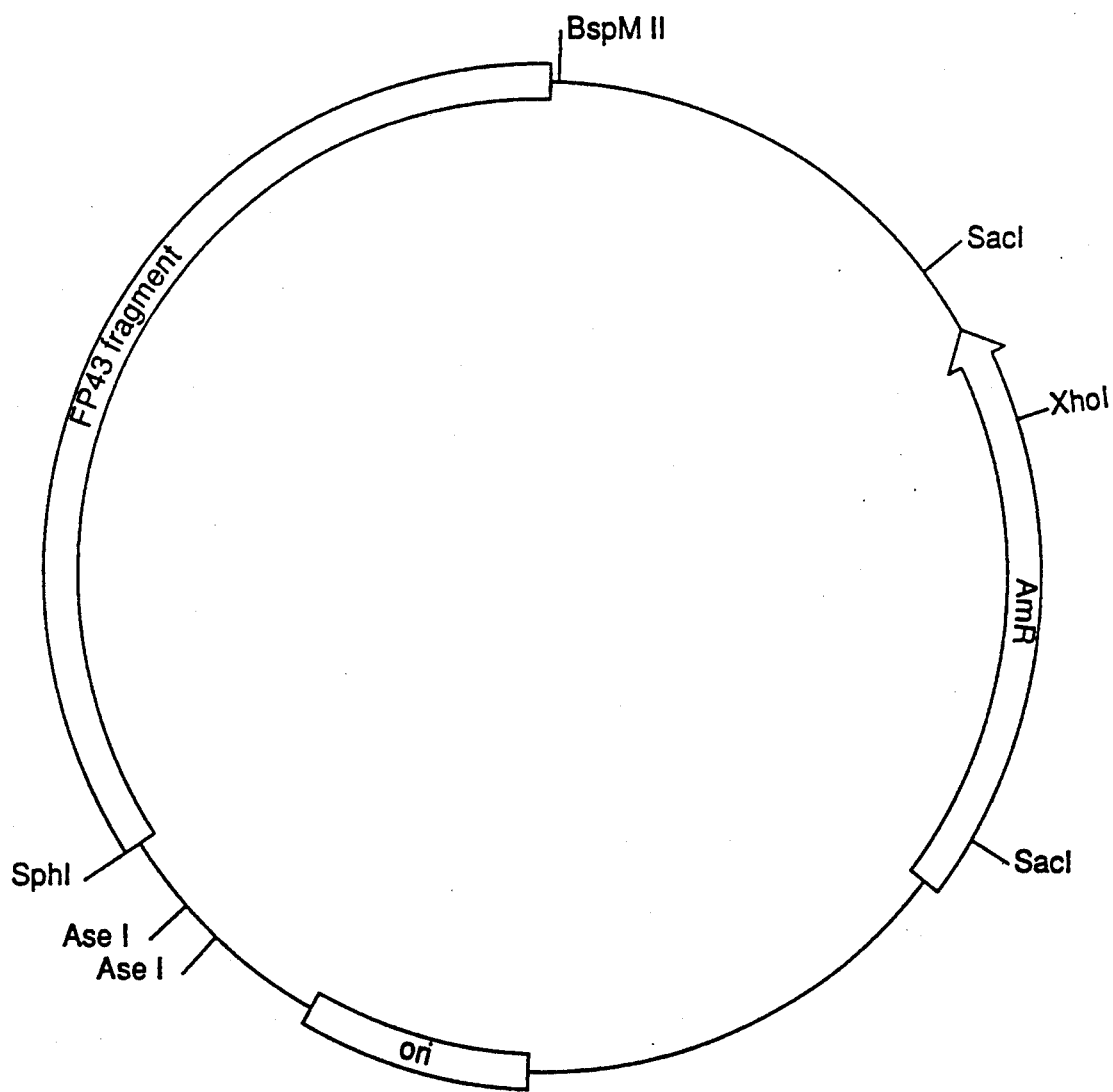
FIG. 7 is a restriction site and function map of plasmid pKC761.

Plasmid pKC761 was prepared by deleting the ~1.5 kb Fsp I fragment from plasmid pKC721. A restriction site and function map of plasmid pKC761 is provided in FIG. 7.

Plasmid pKC721 was prepared by transforming *E. coli* JM109 with plasmid pKC721 DNA (Example 9). The transformation procedure was performed in substantial accordance with the method of Example 6 except that *E. coli* JM109 were used instead of *E. coli* DH5α and plasmid pKC721 was used instead of the plasmid pKC684/pKC685 ligation mixture. Transformants were selected on TY agar containing apramycin (100 μg/ml).

Plasmid pKC721 was purified on a cesium chloride gradient in substantial accordance with the teachings of Example 5. 2 μg of cesium chloride purified plasmid pKC721 were digested with 12 U Fsp I in a total volume of 20 μl. Fsp I digestion buffer consists of 50 mM NaCl, 10 mM Tris-HCl (pH=7.4), 10 mM MgCl₂, 10 mM DTT, and 100 μg/ml bovine serum albumin (Fsp I digestion buffer).

The Fsp I digest was separated using agarose gel electrophoresis (NuSieve GTG) and the ~4 kb fragment was harvested from the gel as an approximately 40 μl gel plug. The gel was melted and the ~4 kb DNA was ligated in substantial accordance with the method taught in Example 7. Plasmid pKC761 results from the ligation of the ~4 kb DNA fragment.

*Streptomyces griseofuscus* C581 was transformed with plasmid pKC761 in substantial accordance with the protoplasting and transformation methods taught in Example 10. Transformants were selected on R2YE containing apramycin (25 μg/ml) as taught in Example 10. Isolated colonies were cultured and plasmids were isolated therefrom in substantial accordance with the teachings of Example 10.

Plasmid pKC761 DNA was then transformed into *E. coli* (JM109) and transformants were selected on TY containing apramycin (100 μg/ml). The transformation of *E. coli* is described in Example 6. Plasmid pKC761 was isolated in substantial accordance with the teaching of Example 5. Restriction endonuclease mapping confirmed the structure of plasmid pKC761. A restriction site and function map of plasmid pKC761 is provided in FIG. 7.

EXAMPLE 13

Southern Blot Analysis of *S. griseofuscus* Transformants

A. Preparation of the Cultures

Ten ml cultures of S. griseofuscus C581, C581/pKC702, *S. griseofuscus* C581/pKC684 and *Streptomyces griseofuscus*/pKC-XS were prepared by inoculating 10 ml of TSB with 0.1 ml of corresponding cultures prepared as previously set forth. The cultures are incubated overnight at 30° C. in a gyratory water bath.

B. Restriction Endonuclease Digestion and Gel Electrophoresis

Each culture prepared in 13(A) was treated as follows. 10 µl of the total DNA prepared as taught in Example 10 was digested with 12 U of Sma I for 1 hour at 25° C. in a 20 µl final volume comprising 20 mM KCl, 6 mM Tris-HCl (pH 8.0), 6 mM MgCl$_2$, 6 mM 2-mercaptoethanol, and 100 µg/ml bovine serum albumin.

Plasmids pKC684, pKC702, pKC703 and pKC-XS were purified on cesium chloride gradients in substantial accordance with the teaching of Example 10. Approximately 0.4 µg of each plasmid was digested with 12 U of Sma I using the same volume, digestion buffer, and digestion conditions as described above for total DNA.

Multiple gels of each sample DNA were run to allow hybridization with the panel of probes set forth in Example 13D below.

The Sma I digests prepared above were then electrophoresed on 0.7% agarose (Sigma Type II) gels. Total DNA was applied as 15 µl of the total DNA Sma I digest. Plasmid DNAs were loaded as 1 µl of the Sma I digest. TAE was used as the gel electrophoresis buffer. 50 V were applied and the gels were run overnight. Molecular weights of restriction fragments were determined by comparison to migration distances of standards of known molecular weights.

D. Preparation of Probes

Probes were prepared as follows. Probes were prepared for plasmid pKC702 and plasmid pKC703. The following reagents were added to a 1.5 ml Eppendorf tube (sitting in ice) 1 µl (~0.5 µg) of the relevant plasmid DNA from which the probe is being produced: 5 µl of 10X nick-translation buffer [0.5M Tris-HCl (pH 7.2), 0.1M MgSO$_4$, 1 mM dithiothreitol, and 50 U µg/ml bovine serum albumin]; 1 µl of 1 mM dATP; 1 µl of 1 mM dTTP; 1 µl of 1 mM dGTP; 156 picomoles of $\alpha$ $^{32}$PdCTP; 1 µg of test DNA; and water to achieve a final volume of 45 µl. The dideoxy nucleoside triphosphates (dATP, dTTP, dGTP, and $\alpha$ $^{32}$PdCTP) were purchased as aqueous solutions from the DuPont Company, NEN Research Products, Customer Services, 549 Albany Street, Boston Mass. 02118. A 5 µl volume of a solution containing 5 U of *E. coli* DNA polymerase I and 5 U of DNase I were added. The nick translation mixture was gently mixed, then incubated on ice for 1 hour. 2 µl of 0.5M EDTA were added to terminate the reaction.

The specific activity of the plasmid DNA probe was determined after separating the nick translated DNA probes from unincorporated nucleoside triphosphates by trichloroacetic acid (TCA) precipitation.

E. Transfer of DNA Onto S & S Nytran Membranes

(1) DNA Fractionation

DNA was fractionated on an 0.7% agarose gel. A Tris-acetate (TAE) buffer consisting of 40 mM Tris-acetate and 1 mM EDTA, ph 8.0, was used as the electrophoresis buffer. DNA fragments were stained after electrophoresis with 0.5 µg/ml ethidium bromide.

(2) Membrane preparation for DNA transfer

S & S NYTRAN nylon membranes were purchased from Schleicher and Schuell, Inc, Keene, N.H. 03431 and used as the preferred hybridization membranes. The membranes were prepared by floating them in deionized H$_2$O, then submerging them to wet thoroughly. The membranes were rinsed and soaked in water until needed.

(3) DNA Fragmentation

DNA fragmentation was accomplished by immersion of the gels in 0.25N HCl for 8 minutes at room temperature.

(4) Gel Equilibration in Transfer Buffer

The gel was rinsed in deionized water, then soaked in two changes of 0.4M NaOH for 30 minutes. A 2 fold volume of 0.4M NaOH per volume of gel is preferred.

(5) DNA Transfer to NYTRAN Membranes by Capillary Action

DNA was transferred from the 0.7% agarose gel to the NYTRAN membrane by capillary action. 0.4M NaOH was used as the transfer buffer. 3 pieces of Whatman blotting paper were cut to generate blotting paper 6" larger than the gel. The blotting paper was saturated with transfer buffer and placed on a glass plate. The blotting paper-glass plate was placed in the bottom of a glass baking dish and the 0.7% agarose gel was then placed on the blotting paper. The NYTRAN membrane was placed atop the gel and 3 more pieces of blotting paper (precut to fit the gel) were placed atop the NYTRAN membrane. Parafilm ® strips were placed along the gel to prevent contact between the upper and lower layers of blotting paper. A one inch stack of paper towels was placed atop the upper layer of blotting paper. A volume of transfer buffer sufficient to saturate the lower layer of blotting paper. The transfer procedure was completed by overnight incubation at room temperature.

(6) Membrane Preparation for Hybridization

After the transfer process was completed, the membrane was blotted, washed twice in SSPE (0.18M NaCl, 10 mM phosphate buffer (pH 7.7), 1 mM EDTA) at room temperature for 5 minutes. The membrane was then wiped with a latex-gloved finger to remove any agarose retained on the membrane from its contacting the gel during the capillary transfer.

(7) Hybridization Protocol (A) Prehybridization - The membrane (from step 6) was placed in a heat-sealable polyethylene bag and approximately 0.25 ml/cm$^2$ prehybridization buffer was added. Prehybridization buffer consists of 5X SSPE, 5X Denhardt's solution, 1% SDS, 20 µg/ml salmon testes DNA (fragmented, denatured, and phenol extracted prior to use), and 10 µg/ml Poly-A RNA. Denhardt's solution consists of 0.02% ficoll, 0.02% polyvinylpyrrolidone, and 0.02% bovine serum albumin. Salmon testes DNA was purchased from Sigma Chemical Co., St. Louis, Mo. 63178. The membrane was incubated in prehybridization buffer for 2 hours at 42° C.

(B) The pre-hybridization solution was removed from the container. Hybridization buffer was then added. Hybridization buffer consists of 5X SSPE, 1% SDS, 50% formamide (pH 7.4), 20 μg/ml fragmented, denatured DNA, and 10% dextran sulfate 500.

(C) Hybridization - Probes were prepared as described above (Example 14D). Probes were denatured by boiling in TE buffer for 5 minutes, then immediately placing them on ice. A volume of each probe, pre-calculated to contain $10^6$ cpm/probe, was then added to each membrane being probed.

EXAMPLE 14

Construction of Plasmid pKC-XS

Plasmid pKC-XS was constructed by insertion of the ~0.8 kb Sac II fragment of plasmid pKC721 into Sma I digested plasmid pKC702. A restriction site and function map of plasmid pKC-XS is provided in FIG. 8.

(A) Vector Preparation

1 μg of plasmid pKC702 was digested with 10 U Sma I (New England Biolabs) in a 20 μl total reaction volume comprising 20 mM KCl, 6 mM Tris-HCl, pH 8.0, 6 mM MgCl$_2$, 6 mM 2-mercaptoethanol, and 100 μg/ml bovine serum albumin, for 1 hour at 37° C.

The Sma I-digested plasmid pKC702 termini were dephosphorylated to prevent self-ligation. The dephosphorylated, Sma I-digested pKC702 was extracted with phenol, extracted with Sevag, ethanol precipitated, and resuspended in 10 μl TE.

(B) Insert Preparation

5 μg of plasmid pKC721 was digested with 60 U Sac II (New England Biolabs) in a 100 μl total reaction volume comprising: 10 mM Tris-HCl (pH 7.5), 10 mM MgCl$_2$, 10 mM DTT, and 100 μg/ml bovine serum albumin for 1 hour at 37° C.

The Sac II digested pKC721 was electrophoresed on a 1% NuSieve GTG agarose gel using TAE as the electrophoresis buffer. The ~0.8 kb Sac II fragment was harvested from the gel as an ~60 μl plug. 40 μl of TE was added to the plug. The gel plug containing the ~0.8 kb Sac II fragment of pKC721 was melted by heating to 70° C. The ~0.8 kb fragment was purified by phenol extraction, Sevag extraction, and ethanol precipitation. The resultant DNA pellet consisting of the ~0.8 kb Sac II fragment of pKC721 was resuspended in 10 μl of TE.

(C) Ligation of (A) and (B) to Produce Plasmid pKC-XS

1 μl of the Sma I-digested and dephosphorylated pKC702 (step A) was combined with 10 μl of the 0.8 kb Sac II fragment of pKC721 (step B). These components were then ligated by addition of 2 μl 0.2M DTT, 2 μl 10X ligase buffer [0.5M Tris-HCl (pH 7.8), 100 mM MgCl$_2$], 2 μl 10 mM ATP, 2 μl H$_2$O, and 2 μl T4 DNA ligase (New England Biolabs) and incubation of the ligation mixture overnight at 15° C.

(D) Transformation of E. coli With Plasmid pKC-XS

The ligation mixture was heated to 70° C. for 10 minutes to inactivate the T4 ligase. 5 μl of the ligation mixture was used to transform E. coli JM109 in substantial accordance with the transformation protocol set forth in Example 7. Transformants were selected on TY agar containing 100 μg/ml apramycin. Isolated colonies were used to prepare plasmid pKC-XS as described in Example 6C.

(E) Restriction Endonuclease Mapping

Restriction endonuclease mapping using a double digest of EcoRI and Hind III (both from New England Biolabs) confirmed the structure of plasmid pKC-XS. The digestion mixture contained ~3 μg of plasmid DNA, 50 mM NaCl, 50 mM Tris-HCl (pH 8.0), 10 mM MgCl$_2$, and 100 μg/ml bovine serum albumin.

Digestion of plasmid pKC-XS with EcoRI and Hind III results in a 2.7 kb fragment and a 3.6 kb fragment. Plasmids lacking the ~0.8 kb Sac II fragment yielded an ~2.7 fragment and an ~2.8 fragment when "double-digested" with EcoRI and Hind III. Fragment sizes were determined by electrophoresis in 1% agarose using TAE as the electrophoresis buffer.

(F) Production of pKC-XS

Production of large amounts of pKC-XS was accomplished by culturing E. coli JM109/pKC-XS in TY containing 100 μg/ml apramycin. Plasmid pKC-XS was harvested and purified on a cesium chloride gradient in substantial accordance with the teachings of Example 5B.

EXAMPLE 15

Challenging S. Griseofuscus Transformants with Phage FP43

A. Preparation of Cultures

S. griseofuscus C581 cultures were transformed with 1 μg preparations of either plasmid pKC684 or plasmid pKC702. Preparation of plasmid pKC684 was taught in Example 5. Preparation of plasmid pKC702 was taught in Example 7. Transformation of S. griseofuscus and selection of transformants on R2YE containing apramycin (25 μg/ml) were taught in Example 10.

Transformation and transformant selection were performed in substantial accordance with the teachings of Example 10. Isolated colonies of plasmid pKC702 and plasmid pKC684 transformants were cultured in TSB containing apramycin (25 μg/ml) for 3 days at 30° C. to provide sufficient material for the phage FP43 challenge.

Preparation of Phage FP43 Lysates

B. Phage Isolation

Phage isolation was performed in substantial accordance with the teachings of Example 1.

C. Challenging Streptomyces Transformants With Phage FP43

Overnight cultures of Streptomyces griseofuscus C581, S. griseofuscus C581/pKC684, and S. griseofuscus/C581/pKC702 and S. griseofuscus/pKC-XS were prepared. NCA plates containing 25 μg/ml apramycin were "seeded" with 0.1 ml of each culture. Phage FP43 lysates (Example 1) in NCB were prepared. Log 10 dilutions ($10^0$-$10^8$) were prepared. Approximately 10 ml of each dilution was added to a representative plate of the series of "seeded" NCA plates containing apramycin (25 μg/ml) prepared above. The plates were allowed to dry for 15 minutes, after which they were incubated at 34° C. overnight. The plates were "scored" for plaques or absence or variation of plaques to determine whether *S. griseofuscus* transformants comprising phage FP43-derived DNA sequences conferred the plaque inhibition (pin) phenotype. *S. griseofuscus* transformants comprising the pin sequence were immune to lysis by phage FP43. The ~0.8 kb Sac II restriction fragment of phage FP43 protected *S. griseofuscus* transformants from phage FP43 lysis.

We claim:

1. A recombinant DNA vector that comprises the pin sequence of phage FP43, said sequence residing on about an 0.8 kb Sac II restriction fragment of phage FP43, or a subfragment of said restriction fragment which has the plaque inhibition phenotype.

2. The recombinant DNA vector of claim 1 that comprises the ~0.8 kb Sac II restriction fragment of phage FP43.

3. The recombinant DNA vector of claim 1 that is plasmid pKC-XS.

4. The recombinant DNA vector of claim 1 that is plasmid pKC684.

5. The recombinant DNA vector of claim 1 that is plasmid pKC685.

6. The microorganism transformed with a recombinant DNA vector of claim 1.

7. The organism of claim 6 that is selected from the group consisting of Streptomyces, Chainia, Saccharopolyspora, and Streptoverticillium.

8. The organism of claim 7 that is a species of the genus Streptomyces.

9. The organism of claim 8 that is *Streptomyces griseofuscus*.

10. The organism of claim 9 that is *Streptomyce griseofuscus*/pKC-XS.

11. The organism of claim 9 that is *Streptomyces griseofuscus*/pKC684.

12. The organism of claim 9 that is *Streptomyces griseofuscus*/pKC685.

13. A microorganism of claim 7 which is transduced with a recombinant DNA vector comprising an hft sequence and a DNA sequence of interest.

* * * * *